(12) United States Patent
Gong et al.

(10) Patent No.: US 6,677,144 B2
(45) Date of Patent: Jan. 13, 2004

(54) ISOLATED NUCLEIC ACID MOLECULES ENCODING HUMAN PYRUVATE DEHYDROGENASE E1-ALPHA SUBUNIT PROTEINS

(75) Inventors: Fangcheng Gong, Germantown, MD (US); Karen A. Ketchum, Germantown, MD (US); Valentina DiFrancesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 71 days.

(21) Appl. No.: 09/901,151

(22) Filed: Jul. 10, 2001

(65) Prior Publication Data

US 2002/0127672 A1 Sep. 12, 2002

Related U.S. Application Data

(63) Continuation-in-part of application No. 09/799,344, filed on Mar. 6, 2001, now abandoned.

(51) Int. Cl.[7] .......................... C12N 9/04; C12N 15/00; C12N 1/20; C07H 21/04
(52) U.S. Cl. ................. 435/190; 435/320.1; 435/252.3; 435/325; 536/23.2; 536/23.5
(58) Field of Search ............................. 536/23.1, 23.2, 536/23.5; 435/320.1, 325, 252.3, 232, 190

(56) References Cited

U.S. PATENT DOCUMENTS 5,283,173 A    2/1994  Fields et al.
5,837,832 A   11/1998  Chee et al.

OTHER PUBLICATIONS

Williams et al. (1998) Biochemistry 37:7096–7102.*
Broun et al. (1998) Science 282:1315–1317.*
Seffernick et al. (2001) J Bacteriol 183:2405–2410.*
Database GenBank Accession No. L13318 (Jan. 8, 1995).*
Brown et al. "Transfection Screening for Primary Defects in the Pyruvate Dehydrogenase E1–alpha Subunit Gene." Hum. Mol. Gen. 1997. vol. 6, No. 8, pp. 1361–1367.
De Meirleir et al. "Isolation of a Full–Length Complementary DNA Coding for Human E1–alpha Subunit of the Pyruvate Dehydrogenase Complex." J. Biol. Chem. Feb. 5, 1988, vol. 263, No. 4, pp. 1991–1995.
Houdebine L. "The Methods to Generate Transgenic Animals and to Control Transgene Expression." J. Biotech. 2002. vol. 98. pp. 145–160.
International Search reported dated Apr. 30, 2003 for PCT/US02/06696.

* cited by examiner

Primary Examiner—Rebecca E. Prouty
Assistant Examiner—David J. Steadman
(74) Attorney, Agent, or Firm—Celera Genomics; Justin D. Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

24 Claims, 17 Drawing Sheets

```
   1 TGCTGGGGCA CCTGAAGGAG ACTTGGGGGC ACCCGCGTCG TGCCTCCTGG
  51 GTTGTGAGGA GTCGCCGCTG CCGCCACTGC CTGTGCTTCA TGAGGAAGAT
 101 GCTCGCCGCC GTCTCCCGCG TGCTGTCTGG CGCTTCTCAG AAGCCGGCAA
 151 GCAGAGTGCT GGTAGCATCC CGTAATTTTG CAAATGATGC TACATTTGAA
 201 ATTAAGAAAT GTGACCTTCA CCGGCTGGAA GAAGGCCCTC CTGTCACAAC
 251 AGTGCTCACC AGGGAGGATG GGCTCAAATA CTACAGGATG ATGCAGACTG
 301 TACGCCGAAT GGAGTTGAAA GCAGATCAGC TGTATAAACA GAAAATTATT
 351 CGTGGTTTCT GTCACTTGTG TGATGGTCAG TTTCTCCTTC CTCTAACACA
 401 GGAAGCTTGC TGTGTGGGCC TGGAGGCCGG CATCAACCCC ACAGACCATC
 451 TCATCACAGC CTACCGGGCT CACGGCTTTA CTTTCACCCG GGGCCTTTCC
 501 GTCCGAGAAA TTCTCGCAGA GCTTACAGGA CGAAAGGAG GTTGTGCTAA
 551 AGCGAAAGGA GGATCGATGC ACATGTATGC CAAGAACTTC TACGGGGGCA
 601 ATGGCATCGT GGGAGCGCAG GTGCCCCTGG GCGCTGGGAT TGCTCTAGCC
 651 TGTAAGTATA ATGGAAAAGA TGAGGTCTGC CTGACTTTAT ATGGCGATGG
 701 TGCTGCTAAC CAGGGCCAGA TATTCGAAGC TTACAACATG GCAGCTTTGT
 751 GGAAATTACC TTGTATTTTC ATCTGTGAGA ATAATCGCTA TGGAATGGGA
 801 ACGTCTGTTG AGAGAGCGGC AGCCAGCACT GATTACTACA AGAGAGGCGA
 851 TTTCATTCCT GGGCTGAGAG TGGATGGAAT GGATATCCTG TGCGTCCGAG
 901 AGGCAACAAG GTTTGCTGCT GCCTATTGTA GATCTGGGAA GGGGCCCATC
 951 CTGATGGAGC TGCAGACTTA CCGTTACCAC GGACACAGTA TGAGTGACCC
1001 TGGAGTCAGT TACCGTACAC GAGAAGAAAT TCAGGAAGTA AGAAGTAAGA
1051 GTGACCCTAT TATGCTTCTC AAGGACAGGA TGGTGAACAG CAATCTTGCC
1101 AGTGTGGAAG AACTAAAGGA AATTGATGTG GAAGTGAGGA AGGAGATTGA
1151 GGATGCTGCC CAGTTTGCCA CGGCCGATCC TGAGCCACCT TTGGAAGAGC
1201 TGGGCTACCA CATCTACTCC AGCGACCCAC CTTTTGAAGT TCGTGGTGCC
1251 AATCAGTGGA TCAAGTTTAA GTCAGTCAGT TAAGGGGAGG AGAAGGAGAG
1301 GTTATACCTT CAGGGGGCTA CCAGACAGTG TTCTCAACTT GGTTAAGGAG
1351 GAAGAAAACC CAGTCAATGA AATTCAATGA AATTCTTGGA AACTTCCATT
1401 AAGTGTGTAG ATTGAGCAGG TAGTAATTGC ATGCAGTTTG TACATTAGTG
1451 CATTAAAAGA TGAATTATTG AGTGCTTAAA AAAAAAAAA AAAAAAAAA
1501 AAAAAAAAAA AAAAAAAAAA AAAAAAAAAA AAAAAAAAAA AAAAA  (SEQ ID NO:1)
```

FEATURES:
5'UTR:        1-89
Start Codon:  90
Stop Codon:   1281
3'UTR:        1284

Homologous proteins:
Top 10 BLAST Hits

|  |  | Score | E |
|---|---|---|---|
| CRA\|18000004925454 | /altid=gi\|387011 /def=gb\|AAA60055.1\| (J03503... | 846 | 0.0 |
| CRA\|18000004920128 | /altid=gi\|4505685 /def=ref\|NP_000275.1\| pyru... | 793 | 0.0 |
| CRA\|18000004938217 | /altid=gi\|6679261 /def=ref\|NP_032836.1\| pyru... | 783 | 0.0 |
| CRA\|18000004939896 | /altid=gi\|66035 /def=pir\|\|DERTP1 pyruvate de... | 782 | 0.0 |
| CRA\|18000004949905 | /altid=gi\|129064 /def=sp\|P26284\|ODPA_RAT PYR... | 779 | 0.0 |
| CRA\|18000004885327 | /altid=gi\|266686 /def=sp\|P29804\|ODPA_PIG PYR... | 777 | 0.0 |
| CRA\|18000004969398 | /altid=gi\|443580 /def=prf\|\|1917268A pyruvate... | 729 | 0.0 |
| CRA\|18000005012775 | /altid=gi\|1079460 /def=pir\|\|A49360 pyruvate ... | 718 | 0.0 |
| CRA\|18000004884262 | /altid=gi\|1709452 /def=sp\|P52900\|ODPA_SMIMA ... | 709 | 0.0 |
| CRA\|18000004925713 | /altid=gi\|4885543 /def=ref\|NP_005381.1\| pyru... | 680 | 0.0 |

FIGURE 1, page 1 of 2

```
BLAST hits to dbEST :
gi|10991237 /dataset=dbest /taxon=96...  1354  0.0
gi|14051054 /dataset=dbest /taxon=960... 1415  0.0
gi|14076211 /dataset=dbest /taxon=960... 1382  0.0
gi|11251518 /dataset=dbest /taxon=96...  1340  0.0
gi|13914836 /dataset=dbest /taxon=960... 1298  0.0
gi|2539160  /dataset=dbest /taxon=9606 ...1037 0.0
gi|3214685  /dataset=dbest /taxon=9606 ...1015 0.0
gi|5933458  /dataset=dbest /taxon=9606 ... 955 0.0
gi|4988948  /dataset=dbest /taxon=9606 ... 842 0.0
gi|4900594  /dataset=dbest /taxon=9606 ... 856 0.0
gi|4534604  /dataset=dbest /taxon=9606 ... 819 0.0
gi|7455087  /dataset=dbest /taxon=9606... 789  0.0
```

EXPRESSION INFORMATION FOR MODULATORY USE:
library source:
Expression information from BLAST dbEST hits:
gi|10991237 Neuronal precursor cells-teratocarcinoma
gi|14051054 skin
gi|14076211 skin melanotic melanoma, high MDR (cell line)
gi|11251518 muscle rhabdomyosarcoma
gi|13914836 brain neuroblastoma, cell line
gi|2539160  whole brain
gi|3214685  breast
gi|5933458  stomach
gi|4988948  pancreas - adenocarcinoma
gi|4900594  uterus - serous papillary carcinoma, high grade
gi|4534604  brain - anaplastic oligodendroglioma
gi|7455087  colon - moderately-differentiated adenocarcinoma Tissue source of cDNA clone:
Fetal whole brain

```
  1 MRKMLAAVSR VLSGASQKPA SRVLVASRNF ANDATFEIKK CDLHRLEEGP
 51 PVTTVLTRED GLKYYRMMQT VRRMELKADQ LYKQKIIRGF CHLCDGQFLL
101 PLTQEACCVG LEAGINPTDH LITAYRAHGF TFTRGLSVRE ILAELTGRKG
151 GCAKAKGGSM HMYAKNFYGG NGIVGAQVPL GAGIALACKY NGKDEVCLTL
201 YGDGAANQGQ IFEAYNMAAL WKLPCIFICE NNRYGMGTSV ERAAASTDYY
251 KRGDFIPGLR VDGMDILCVR EATRFAAAYC RSGKGPILME LQTYRYHGHS
301 MSDPGVSYRT REEIQEVRSK SDPIMLLKDR MVNSNLASVE ELKEIDVEVR
351 KEIEDAAQFA TADPEPPLEE LGYHIYSSDP PFEVRGANQW IKFKSVS  (SEQ ID NO:2)
```

FEATURES:
Functional domains and key regions:
[1] PDOC00005 PS00005 PKC_PHOSPHO_SITE
Protein kinase C phosphorylation site Number of matches: 7
```
    1      16-18  SQK
    2      70-72  TVR
    3     137-139 SVR
    4     146-148 TGR
    5     282-284 SGK
    6     293-295 TYR
    7     307-309 SYR
```

[2] PDOC00006 PS00006 CK2_PHOSPHO_SITE
Casein kinase II phosphorylation site

Number of matches: 7
```
    1      57-60  TRED
    2     137-140 SVRE
    3     238-241 TSVE
    4     300-303 SMSD
    5     310-313 TREE
    6     319-322 SKSD
    7     338-341 SVEE
```

[3] PDOC00008 PS00008 MYRISTYL
N-myristoylation site

Number of matches: 7
```
    1     110-115 GLEAGI
    2     114-119 GINPTD
    3     151-156 GCAKAK
    4     172-177 GIVGAQ
    5     181-186 GAGIAL
    6     183-188 GIALAC
    7     235-240 GMGTSV
```

[4] PDOC00009 PS00009 AMIDATION
Amidation site

```
          146-149 TGRK
```

[5] PDOC00016 PS00016 RGD
Cell attachment sequence

```
          252-254 RGD
```

Membrane spanning structure and domains:

| Helix | Begin | End | Score | Certainty |
|---|---|---|---|---|
| 1 | 169 | 189 | 1.097 | Certain |

FIGURE 2, page 1 of 4

BLAST Alignment to Top Hit:
```
>CRA|18000004925454 /altid=gi|387011 /def=gb|AAA60055.1| (J03503)
            pyruvate dehydrogenase E1-alpha precursor [Homo sapiens]
            /org=Homo sapiens /taxon=9606 /dataset=nraa /length=414
          Length = 414

Score =  846 bits (2163), Expect = 0.0
 Identities = 411/421 (97%), Positives = 411/421 (97%)
 Frame = +3

Query: 18    ETWGHPRRASWVVRSRRCRHCLCFMRKMLAAVSRVLSGASQKPASRVLVASRNFANDATF 197
             ETWGHPRRASWVVRSRRCRHCLCFMRKMLAAVSRVLSGASQKPASRVLVASRNFANDATF
Sbjct: 1     ETWGHPRRASWVVRSRRCRHCLCFMRKMLAAVSRVLSGASQKPASRVLVASRNFANDATF 60

Query: 198   EIKKCDLHRLEEGPPVTTVLTREDGLKYYRMMQTVRRMELKADQLYKQKIIRGFCHLCDG 377
             EIKKCDLHRLEEGPPVTTVLTREDGLKYYRMMQTVRRMELKADQLYKQKIIRGFCHLCDG
Sbjct: 61    EIKKCDLHRLEEGPPVTTVLTREDGLKYYRMMQTVRRMELKADQLYKQKIIRGFCHLCDG 120

Query: 378   QFLLPLTQEACCVGLEAGINPTDHLITAYRAHGFTFTRGLSVREILAELTGRKGGCAKAK 557
             Q      EACCVGLEAGINPTDHLITAYRAHGFTFTRGLSVREILAELTGRKGGCAK K
Sbjct: 121   Q-------EACCVGLEAGINPTDHLITAYRAHGFTFTRGLSVREILAELTGRKGGCAKGK 173

Query: 558   GGSMHMYAKNFYGGNGIVGAQVPLGAGIALACKYNGKDEVCLTLYGDGAANQGQIFEAYN 737
             GGSMHMYAKNFYGGNGIVGAQVPLGAGIALACKYNGKDEVCLTLYGDGAANQGQIFEAYN
Sbjct: 174   GGSMHMYAKNFYGGNGIVGAQVPLGAGIALACKYNGKDEVCLTLYGDGAANQGQIFEAYN 233

Query: 738   MAALWKLPCIFICENNRYGMGTSVERAAASTDYYKRGDFIPGLRVDGMDILCVREATRFA 917
             MAALWKLPCIFICENNRYGMGTSVERAAASTDYYKRGDFIPGLRVDGMDILCVREATRFA
Sbjct: 234   MAALWKLPCIFICENNRYGMGTSVERAAASTDYYKRGDFIPGLRVDGMDILCVREATRFA 293

Query: 918   AAYCRSGKGPILMELQTYRYHGHSMSDPGVSYRTREEIQEVRSKSDPIMLLKDRMVNSNL 1097
             AAYCRSGKGPILMELQTYRYHGHSMSDPGVSYRTREEIQEVRSKSDPIMLLKDRMVNSNL
Sbjct: 294   AAYCRSGKGPILMELQTYRYHGHSMSDPGVSYRTREEIQEVRSKSDPIMLLKDRMVNSNL 353

Query: 1098  ASVEELKEIDVEVRKEIEDAAQFATADPEPPLEELGYHIYSSDPPFEVRGANQWIKFKSV 1277
             ASVEELKEIDVEVRKEIED AQFA ADPEPPLEELGYHIYSSDPPFEVRGANQWIKFKSV
Sbjct: 354   ASVEELKEIDVEVRKEIEDPAQFAAADPEPPLEELGYHIYSSDPPFEVRGANQWIKFKSV 413

Query: 1278  S 1280
             S
Sbjct: 414   S 414     (SEQ ID NO:4)

>CRA|18000004920128 /altid=gi|4505685 /def=ref|NP_000275.1| pyruvate
            dehydrogenase (lipoamide) alpha 1; Pyruvate
            dehydrogenase, E1-alpha polypeptide-1 [Homo sapiens]
            /org=Homo sapiens /taxon=9606 /dataset=nraa /length=390
          Length = 390

Score =  793 bits (2025), Expect = 0.0
 Identities = 389/397 (97%), Positives = 389/397 (97%)
 Frame = +3

Query: 90    MRKMLAAVSRVLSGASQKPASRVLVASRNFANDATFEIKKCDLHRLEEGPPVTTVLTRED 269
             MRKMLAAVSRVLSGASQKPASRVLVASRNFANDATFEIKKCDLHRLEEGPPVTTVLTRED
Sbjct: 1     MRKMLAAVSRVLSGASQKPASRVLVASRNFANDATFEIKKCDLHRLEEGPPVTTVLTRED 60

Query: 270   GLKYYRMMQTVRRMELKADQLYKQKIIRGFCHLCDGQFLLPLTQEACCVGLEAGINPTDH 449
             GLKYYRMMQTVRRMELKADQLYKQKIIRGFCHLCDGQ       EACCVGLEAGINPTDH
Sbjct: 61    GLKYYRMMQTVRRMELKADQLYKQKIIRGFCHLCDGQ-------EACCVGLEAGINPTDH 113
```

FIGURE 2, page 2 of 4

```
Query:  450  LITAYRAHGFTFTRGLSVREILAELTGRKGGCAKAKGGSMHMYAKNFYGGNGIVGAQVPL  629
             LITAYRAHGFTFTRGLSVREILAELTGRKGGCAK KGGSMHMYAKNFYGGNGIVGAQVPL
Sbjct:  114  LITAYRAHGFTFTRGLSVREILAELTGRKGGCAKGKGGSMHMYAKNFYGGNGIVGAQVPL  173

Query:  630  GAGIALACKYNGKDEVCLTLYGDGAANQGQIFEAYNMAALWKLPCIFICENNRYGMGTSV  809
             GAGIALACKYNGKDEVCLTLYGDGAANQGQIFEAYNMAALWKLPCIFICENNRYGMGTSV
Sbjct:  174  GAGIALACKYNGKDEVCLTLYGDGAANQGQIFEAYNMAALWKLPCIFICENNRYGMGTSV  233

Query:  810  ERAAASTDYYKRGDFIPGLRVDGMDILCVREATRFAAAYCRSGKGPILMELQTYRYHGHS  989
             ERAAASTDYYKRGDFIPGLRVDGMDILCVREATRFAAAYCRSGKGPILMELQTYRYHGHS
Sbjct:  234  ERAAASTDYYKRGDFIPGLRVDGMDILCVREATRFAAAYCRSGKGPILMELQTYRYHGHS  293

Query:  990  MSDPGVSYRTREEIQEVRSKSDPIMLLKDRMVNSNLASVEELKEIDVEVRKEIEDAAQFA  1169
             MSDPGVSYRTREEIQEVRSKSDPIMLLKDRMVNSNLASVEELKEIDVEVRKEIEDAAQFA
Sbjct:  294  MSDPGVSYRTREEIQEVRSKSDPIMLLKDRMVNSNLASVEELKEIDVEVRKEIEDAAQFA  353

Query:  1170 TADPEPPLEELGYHIYSSDPPFEVRGANQWIKFKSVS  1280
             TADPEPPLEELGYHIYSSDPPFEVRGANQWIKFKSVS
Sbjct:  354  TADPEPPLEELGYHIYSSDPPFEVRGANQWIKFKSVS  390   (SEQ ID NO:5)

>CRA|18000004938217 /altid=gi|6679261 /def=ref|NP_032836.1| pyruvate
        dehydrogenase E1alpha subunit [Mus musculus] /org=Mus
        musculus /taxon=10090 /dataset=nraa /length=390
        Length = 390

Score =  783 bits (1999), Expect = 0.0
 Identities = 382/397 (96%), Positives = 387/397 (97%)
 Frame = +3

Query:  90   MRKMLAAVSRVLSGASQKPASRVLVASRNFANDATFEIKKCDLHRLEEGPPVTTVLTRED  269
             MRKMLAAVSRVL+G++QKPASRVLVASRNFANDATFEIKKCDLHRLEEGPPVTTVLTRED
Sbjct:  1    MRKMLAAVSRVLAGSAQKPASRVLVASRNFANDATFEIKKCDLHRLEEGPPVTTVLTRED  60

Query:  270  GLKYYRMMQTVRRMELKADQLYKQKIIRGFCHLCDGQFLLPLTQEACCVGLEAGINPTDH  449
             GLKYYRMMQTVRRMELKADQLYKQKIIRGFCHLCDGQ       EACCVGLEAGINPTDH
Sbjct:  61   GLKYYRMMQTVRRMELKADQLYKQKIIRGFCHLCDGQ-------EACCVGLEAGINPTDH  113

Query:  450  LITAYRAHGFTFTRGLSVREILAELTGRKGGCAKAKGGSMHMYAKNFYGGNGIVGAQVPL  629
             LITAYRAHGFTFTRGL VR ILAELTGR+GGCAK KGGSMHMYAKNFYGGNGIVGAQVPL
Sbjct:  114  LITAYRAHGFTFTRGLPVRAILAELTGRRGGCAKGKGGSMHMYAKNFYGGNGIVGAQVPL  173

Query:  630  GAGIALACKYNGKDEVCLTLYGDGAANQGQIFEAYNMAALWKLPCIFICENNRYGMGTSV  809
             GAGIALACKYNGKDEVCLTLYGDGAANQGQIFEAYNMAALWKLPCIFICENNRYGMGTSV
Sbjct:  174  GAGIALACKYNGKDEVCLTLYGDGAANQGQIFEAYNMAALWKLPCIFICENNRYGMGTSV  233

Query:  810  ERAAASTDYYKRGDFIPGLRVDGMDILCVREATRFAAAYCRSGKGPILMELQTYRYHGHS  989
             ERAAASTDYYKRGDFIPGLRVDGMDILCVREAT+FAAAYCRSGKGPILMELQTYRYHGHS
Sbjct:  234  ERAAASTDYYKRGDFIPGLRVDGMDILCVREATKFAAAYCRSGKGPILMELQTYRYHGHS  293

Query:  990  MSDPGVSYRTREEIQEVRSKSDPIMLLKDRMVNSNLASVEELKEIDVEVRKEIEDAAQFA  1169
             MSDPGVSYRTREEIQEVRSKSDPIMLLKDRMVNSNLASVEELKEIDVEVRKEIEDAAQFA
Sbjct:  294  MSDPGVSYRTREEIQEVRSKSDPIMLLKDRMVNSNLASVEELKEIDVEVRKEIEDAAQFA  353

Query:  1170 TADPEPPLEELGYHIYSSDPPFEVRGANQWIKFKSVS  1280
             TADPEPPLEELGYHIYSSDPPFEVRGANQWIKFKSVS
Sbjct:  354  TADPEPPLEELGYHIYSSDPPFEVRGANQWIKFKSVS  390  (SEQ ID NO:6)
```

FIGURE 2, page 3 of 4

Hmmer search results (Pfam):

| Model | Description | Score | E-value | N |
|---|---|---|---|---|
| PF00676 | Dehydrogenase E1 component | 598.5 | 4e-176 | 1 |
| PF01579 | Domain of unknown function | 3.0 | 2.3 | 1 |

Parsed for domains:

| Model | Domain | seq-f | seq-t | hmm-f | hmm-t | score | E-value |
|---|---|---|---|---|---|---|---|
| PF01579 | 1/1 | 28 | 46 .. | 153 | 173 .] | 3.0 | 2.3 |
| PF00676 | 1/1 | 66 | 369 .. | 1 | 327 [] | 598.5 | 4e-176 |

FIGURE 2, page 4 of 4

```
   1 AGTTGTTCCT TCTAACCCAT TGATTTGTTC AATCATGTAT TTAAGTAGGA
  51 CCTATATTTT ACTTGTTCCT TGCTATATCT TCAGTGTGTA GTACAGTGTC
 101 TGACACAAAA TCGGTGCTCA ATAATAGGTG TTGGATGAAT GAGCAAATGA
 151 ATGAATGAAT TCATATTCAT ATGGCCTACA GAGTTCCCGT ACATGCACAA
 201 CCAATATCAC CACCCCGTGG AGATGACTCC CAAATTAATA TTTTTAGCAA
 251 ATGTTCCAGA CTTACAACTC CAACTTCCCG GGGGACATCT TCAGATAGCT
 301 GTGCCACTGC CACCACCAGG TCAACATGTC CCAAACCATT CAGACCAGCT
 351 TTTTCTCCTG AGCTGGACAT CTGGCCTCCA ACCTTTTCAT TCTCTTTTAC
 401 CTTTCATATT CTATCAGCAG CAGCAGCTGC TGAAATCATA CCATGCAAGT
 451 TTCTCACGTC CATCTCTGCC TTTTAATGGC GCCCTCTCAC TCCTTTAAGA
 501 AGTTTTCTTC CACTGCAACA CGATCTCTCA GTCCAGAGTC TGGCCCAGTG
 551 CCCAAATTAT TTCTCTAGCT ATGCTGAGAG CTGGTCATGC TTTGAACTTC
 601 TGCTTTGAAT ACTTTCAGTG ACACTGGGAG AGAATTATCT CATTGGACCA
 651 TTGTCATTGT TAGAAAATTC ATTGTTATGC TGAAATGAAA TGATTTTATT
 701 CACACACACA CACACACACA CACAAAATAG CTCTTCCTCC TGGAACATGA
 751 CTGGCCTGAA AATGTGTGAA GACATATCCA ATCCTCTCTG GTTTTACTGT
 801 TCATCCAATT TTCTGTTCTC CTCCTGGCAG GAGGATTATA TTTCACCTTG
 851 TGGAACTCAG ACATGGTCGG GTAACTAGCT CTGGTCCGTG AAAATTGAGA
 901 GGAAGTGACA TGTGTCACTT CTGGGCAGAA GCTTTGAGAG CCGGTTTAAA
 951 TGATCCCTTT TCTCTTCATC CATGAGACAA GCTAAGTTCC AGAGAGAGGG
1001 TGCCACGCTG TGAGGGACCT GTGTTACGAG TACGATGGCT CGCGTCACTT
1051 CAAATTCTTG AAATCACTGA AATTTGGAGG TCAGTTGTTA CATCATAACC
1101 CAGCCAATTC TAGTTAGCCT GTTTTCTTCC TAACTTCTTT AATCGTTCTT
1151 CATAAGTCAC AATCGCAGCC CCTCACCGTT CTGACCACTG TCCCCTGGAT
1201 TCCACTCAGT TTACTCATTA TCCCCCTTAA AATGTGGAGC CCAAATCTGA
1251 ACCCGGAACC CCAGGTGCAA TCCCACTAGG ACACAACACA ATGGGTTCCT
1301 GAGCCCTTTG ATCCTCTGAA TAGAGCCCCT TGTTGCTTTG GTGTTTTGTC
1351 TCTGTGTGTG CTTTTATCAT CGGCTGAGCC ACGCTGTTAA CTCGCAGTGA
1401 GCCTGTGAAC CAATAACTAG AGAAAAAGA TTTTTCCCAT TGTCCTCTCG
1451 ACATATATTG GGAAACAAAT TTTTTGATCC GCGTTCAAGT AGACAGGGCA
1501 GAACTGTCCA ACTGCTACGT GATCTTTTAA AGACAAAGTT AGTGGCAGAC
1551 CATTTACAGA AACCAGATGT TCTGTCTTTT GGCTCTGAGC ATGCTGCTAA
1601 TCTTCATCAT CTAGTGTACT GAACGAGATG TACTGAACGA GGGCTGCAGA
1651 GCTGCAGCAC CGGCAGGAGT AGGCGCTCGG TAGGACGGGG CCTGCACAAC
1701 CTCCCCGGTA GTCAGCAGAG CGGAATCTAG GAAGGCTCCT TTCCCGCGGC
1751 GCCCTGGAGG CGGGGGCCCC ACCTTCCCAC GCAGGCGCTA TCAAGCCCCG
1801 CCTCCTCACC CGCCCGCGGC GTGGCGTCGG AAAGAGCCCT CAGCCCCTCC
1851 CTCTCTGGCG CTGATACCCA ATGGGCAGCC TCAGGCCTTT AGCGGGGGCG
1901 GGGCACCCCC TGGACGCCGT TCTGGTTGGC CCGCGGCCCG GCGCAGCGCA
1951 TGACGTTATT ACGACTCTGT CACGCCGCGG TGCGACTGAG GCGTGGCGTC
2001 TGCTGGGGCA CCTGAAGGAG ACTTGGGGGC ACCCGCGTCG TGCCTCCTGG
2051 GTTGTGAGGA GTCGCCGCTG CCGCCACTGC CTGTGCTTCA TGAGGAAGAT
2101 GCTCGCCGCC GTCTCCCGCG TGCTGTCTGG CGCTTCTCAG AAGCCGGTGA
2151 GACCTCCCGG GCGGGCCGGG ATGGGCGCG AGTGGGGCTG AGGCGGGGCC
2201 GGAGGGCAGG GCGGGCCAGG CCGGGCCACC CAGAGCGGGG TGGAAGGCGC
2251 CAGGGGAGCC GGGGAGCCTT TACTTCGCCT CCGCGCCCTG CATTCCGTTC
2301 CTGGCCTCGG GAGAAGCGGC ACGGACCGGG ATCACGCCAA GGTCCGTGTG
2351 AACTTCCCCC TTCTCGACAC CCACCTCCCG CCCCGGGCC CAGCTGTGCG
2401 CCAGGCGAAG TCGGTGTGCT CAAGAGGTGC CTGTTGGGTT ACAGGACACG
2451 GAAAGGGTGG CCTCGGCCTC CTTCGAGTCT CCAATTGACC CCACTCATTT
2501 CGGATCTTCT AACTTAATTT CTCTTGACCG AGAGGCTTTG TAATAGCGTA
2551 GAATCTGGAG ACAGGGTGGC TTCGTTCAAA CAGCACCCTC ACCATTGACT
2601 AGCCCTGTGA CCTTGAGCAA GTTTTTAAAC GTCCCGGGGA CCCGGTTTCC
2651 TAAAATGTTT GCTCGAAGTG GAGTTAATCT CTAAATGGAG ATAAGAGTTA
2701 TCTCTGAAAT GTTATCGGTT ATTAAAATGT TATCAGTTAA CTCTAAAATG
2751 GAGATAATAA GAGTCCCCAC CTCTTGGGGT TGTCTTGAGG ATTCAACGAG
2801 TGACACGTGT GGAAACGATT CCAAATAGCA CCTGGCACAT AATCGATAAC
2851 ATGTGTGTTG AATAGTGTTA TTTATTGAGT CTCCAGTTCG GTATACATTT
2901 CTTGAACACC TGTGCTCAGT TCTGAGGCGG GTTCACAGAA GGTCAGCCTC
2951 TTCAGAAACA AACTTCCTCC TCTTCCCTCT CCCTCAACAT CTGAGCTTTT
3001 CTTGGCAGTG AGTTCAGGAG CGCCGAAGCA GAACTCAGAG GACGCTGCCC
3051 TCCCCTCCCC TTACCTACAC ATTCTTAGGG TACAAGTAGC TAAAGCAAAG
3101 AGCAACGATG CTTGAGGGGT GGGGGGTAGA GTTTAGCACT ATTTCATGGC
```

FIGURE 3, page 1 of 11

```
3151 CTCAGCATTT AGAGGTGCCT AACACCTGAG CTAGCATTCT GACCCCCCTA
3201 GGCACAGTGA GGTCGTGTTA ATTGGTGTAA CTGCAGGCCT CGGGATTCTG
3251 GTATTTCCCC CAGGACTTGA TACCGCTCTA CTTAGTACAG GCAAGAGATT
3301 GTCAAAAGGT AAAGAGGTAT GCCCCTCTAG GAATCCTGTT GCCTAAAATA
3351 ATGACAAAAC TGCCGGGTGC GGTGCTCAGG CCTGTAATCC CAGCATTTTG
3401 GGAGGCTGAG GCAGGTGGAT CACCTGAAGG TCAGAAGTTC GAGATCAGCC
3451 TGGCCAACAT GGTGAAACCC CGTCTCTACT AAAAATACAA AATTAGCCGG
3501 TCGTGGTGGC GGGCTCCTGT AATCCCAGCT ACTCGGGAGG CTGAGGCGGG
3551 AGAATAGCCT GAACCCGGGA GCGGAGTTTG CAGTGAGCGG AGATCGTGCC
3601 ATTGCACTAC GGCCTGGGCG ACAAGAAGCA AGAACTCCGT ATTTTAAAAA
3651 AAAAAAAAAA AAAAAAAAAA AAAAGCGTTC CCTTTAGGGA TATCTGTGGG
3701 TAGAGGGCTG TACCGGTAGT TACGGGCTCA GAAACATCCT TCCTTTAGGC
3751 ACCTGATGTA GGTTTTCTTC TTCTTCTGCA AGTCAGGTTC ATTGTTTCCT
3801 GTATCAGTTT GCAGGGTCCC CCCCCCCCG CCACCTTACA GTAGGAAGAA
3851 AATTGAGTTC CAGATATGAA GTCACCTTTG AAAGTGCCCA GGTATCTTTC
3901 CACTTGGTGG TGTAAACTCT TCAGATAATT AGAAGTTTTC TGTGTCACTC
3951 AACTTGTCAT GGACTAATTT AGGAAACATT CCTGAAGCTT TTAAGGATAG
4001 AACTAAAAGT TTCACTTTTA TTTTTTTAAA GGGTGGAATA ATAAACTAAC
4051 GTGTTGACTC TTTGTATTTT GTAATTCTTC ATACTTATGG ATGTCTTTTT
4101 ACTTAACTAT AAGTAACAAA ATAGATCAAC GTTTTAGTTT TTTTATATTA
4151 TACATGTAAA AAGACATTTT GCATATAAGC CTTTCACAAA AATCTTGACA
4201 GTAAACAATA AGCAGTGGCT CACCCAAATT AGGCAGACTT ACTGCACTAG
4251 ACTCCTACCA TCTGTGTGAT ACTCCATGAA GGGAGGGAGA AGGGGAGGGA
4301 GAAGGGTAGG CAGCTGGTCT GATGGCTGTG ACACAAGATA ATCCCCTTAA
4351 CCTCCCAAGA CGCTGTGTGT TTTTTCCTTT TTTATTCTCC CTGGTTTACT
4401 TTCGTTTTGT TTGAGACAGG GTCTCTGTGT CACCCAGGCT GGAGTGCAGT
4451 AGCAGGACAG CTCACTGCAG CCTTAGCCTG CTGGGCTCAA GCGATCCTCC
4501 TGCCTTAGCC TCCTGAGTAG CTGGGAACAC AGGCATGTGC CACCACCACA
4551 CCCAGCCAAT TAAAAAAATT TTTTTTTTAC TAGAGACATG GTCTTGCTAC
4601 GTTGCCCAGT CTGGTCTCCA TCTCCAGGCT CAAGCAGTCC TCCCACCTCG
4651 GCCTCCCAAA GTGCTGGGAT TACTCTCACT CTCTTAAAAC CAGGCAGGTA
4701 GGGAGATTTA TCTCAGGCTT AAAGATTGCC ATTGTCTCAT CAAAGAGTGT
4751 TTGGTGTGAA ACTTTGAAAT GAATATCAAG ATTGTGTTTT TATTTTTGAA
4801 TAAGGTTTAT AGTTTTCATA GTTCTTATTT CATGGAAGAA GATTGAATGC
4851 ATTTAAAATG TTATTTTATT GTTTGCATTT CTGTATGGCT CCTTTTGTGA
4901 GATCTTTACT AGCAATGTTT TGGCTTTATA AGTGGTAGGT AAGAGTTTTA
4951 ATTTACACTG TTAGAATCTG GAATTTTTGA AACGTTTTTC CTCTTTCACA
5001 TGAATGGTTC CTATGTATTT AGGAAGTTAA AGTTTTACTT TTTTTTAATT
5051 AATTTTTTTT TTTAGGCTGG AATGCAGTGG CACAGTCATA GCTCACTGTA
5101 GCCTCAGGTG TGTGCCACCA TACCTGACTA ATTTTTTAAT ATTTATTTTT
5151 GTAGAGATGA GAGTCTCATG TTGCCCAGGC TGGCTTGAA CTCCTGGCTT
5201 CAAGTGGTCC TCCCACCCTG GCCTCCCAAA GTGCTGGGGA TTATAGGTGT
5251 GAGCCATCAT GCCCGGCCTA GTTTTATTT TTTAAATTT GAGTGGGTTG
5301 TTCGTGGTCT CTGTCAGAGA GGAATCCCAT TTAACAGAGA ATCTTTTTAT
5351 GGCTCTCCAG AGAAAATGAA TGGTAAACTT ATCTTTTCAA CAAGCTCTCA
5401 CTCAGAAATG ATACACACAC ACTTCTGATA GGACTTTTAG CTTCTTTAAC
5451 TTTGTTCCTT TCACTCATAT CAGTGGTTCT TATTTTGAG ATACACAGTA
5501 ATGAAGCCAT GGGAGAAAGT ATCTAAGTAG CTTTCTGGCA GTCCTAATCT
5551 TTGCAGGCGC AAGATTACAG GCGCATGCCA CAGCACTGGG CCCCTTCTTG
5601 CTCTTTATTG TATAGCATTA TCCTGCCTCA TTGTTTCAAC TCTAGGATTG
5651 AGAAAGAAGT TACCTTTTCT CTGTTACTGT CGCCTGGCTG GTTTGGACTC
5701 CTGCCTTCCA AAAACTGCAG TTTCTGTAGT TGTATTTGGA AATTTATTTC
5751 ACAATACAAT AAATTTCTGG CCCCACAAAA TATTTATTAA CTGCCAAGAA
5801 TAACACATCT GTTTGATTGC TAAATATAAC CATTGATTTG CTGTTTCACC
5851 TTCTCTCAGC TTTACTTCTT CCCAAATTCC TAAATTTCCT TCACTTTTTC
5901 TGAGATACAT TAGTGGACTG TCTCTGCCTG TAAGTTAACT GAAACACTGA
5951 TTCCTAGTAT TTCAGTTGTT TTCCTCCAGC ACTGTCATTG TCTGTGTTTG
6001 TTGGCTTTGT CCAATAATGG TCTATTGAGG GGTGAAGATA TACGTAATTA
6051 GCTTTCTGCC TATTGGCTTG TACACTCCAG GGTATACTTG GCAGATCAGT
6101 CTTAACTCTT CTCACCAAGA TCAGTCCAGT GCTGGATTAG GTAAGGTATG
6151 AACACATCAG ATGTGCTTTT TATGGAGAAA TCATGTTGGT TTACACGTCA
6201 GTGTGTGAGA ATGTGGCAGA AGGGAGCTAA AATAGTATGA TAATACTACT
6251 GGATAAATTT TGTGGTCTAA CCTAAACCTT AGCCATTACA TAGAATACTT
```

FIGURE 3, page 2 of 11

```
6301 TTGCTGTGAG CAGGTTTGCT CAGTTGTAAA ACTGGAAAGG AATCATTTCT
6351 CACCCCCCGC CTCCAAGCTT TTTACCTCCA AACAGTGACA GCCACCCAAA
6401 CATCAAGAGA ACAGTGTTTC AGAGAACATT TCTACTGGGG CTTCAGGAGG
6451 AGCCTGTCCA AGATTTAGGC TGTTCAAATT ATAAATTATA AAACAGCTGG
6501 CTCAAGCCCA TTGTGTTTAA GTCAGAGAGT GCTAAGTATC TTTTCTTTTG
6551 TCTTGTCTCC CTAAAGTATT TATCTCATAC TTCAATCAAT TTAAATATT
6601 TTTTCTTACA GATCCAATTT GATAGAAGAG TCAAGTTTGC CTAGAGTGGA
6651 GATTAAATCA TAGTTTTATT TGAAGTATAA TTTTGGCTTG CTCAAAATGA
6701 ACAGTATCTG GTTATGACTA AGAATGGCAT GAAAAGGCCA GACGCAGTGG
6751 CTCATGCCTG CAATCCCAGT ACTTTGGGAG GCCAAGGCAG GTGGATCACC
6801 TGAGGTCAGG AGTTGGAGAC CAGCCTGGCC AACATGGTGA AACCCCATCT
6851 CTACTAAAAA TATAAAAATT AGCCGGGCCG TGGTGGTGGG CACCTGTAAT
6901 CCCAGCTACT CGGGAGACTG AGACAGGAGA ATCACTTGA ACCCGGGAAG
6951 CGGAGGTTGC AGTGAGCCGA GATCGCACCA CTGCACTCCA GCCTGGGTGA
7001 TAAAAGCAAA ACTCCGTCTC AAAACAAACA AACAAAAGAA TGGCATAAAC
7051 AGACACAGCT CACAGATGAT CTAGTCTCTT TAGCCACTAA TTTCATTATA
7101 TTCTCACTAT AATTTCTTTG AAAACAAAGG ATGGGTTTGT TTTTTGCCCC
7151 TCTTTGCGCT GCTTGCCTTC AGATGCGGGA TAATCCTGTT TCATTGGCCA
7201 AAGCATGGAT TCATTTTGGA GGCCAAGGAA GATGCAAACA CAGTGCACAG
7251 GGTGGAAGAG AAGCCTATGA ATATGTTGGG GCTTATTAAA TTTCCATAAC
7301 TTCATTCTGA TAACTGATTA TTATACTTTC CAAAATAGCT GACAATTAAA
7351 AAGTACTGAT TGTTTGTAT ATTTTTGTCT TTTAAGGCAA GCAGAGTGCT
7401 GGTAGCATCC CGTAATTTTG CAAATGATGC TACATTTGAA ATTAAGGTAA
7451 GAGTGTTTTA CTTTGTTAAT AATTTTTTCA CAGGTACACT CTGATATACA
7501 GTTTTACCTT TAGAATAGAA CATCTTGATG TTCATGATTA GTCATCATTT
7551 TCTTCTAAAT GTCCAGGATC AGAAGTTCAG AGAAGCTTAT TCAAAAGTTT
7601 GGAATGTAAT TCAGTGAAAT ATTTGAATAA GAAGAGTCTT AGTTGTTTCT
7651 TTGAAGGTTC TTTCAACCTA TAACTCAGTT GGCTTCTAGG GGCTTTCAGT
7701 GAAAATCATC TTAGAAAGAT TTCCTTCCCC CAAGCCCCAT CTCATTGCAC
7751 AGTGAGGTTT ATGGATTTAA GGAACAGAGG CGATATGAAG CATTACTGAT
7801 GTGCTCCTTT GCAGTTTTTC AAGTTCAATA TTATTTGCAA TGGAGTTAGA
7851 TCTTAGAGTG GTCAACAGTG TTTGCAATGT AGTATGTGGA GGATAATAAC
7901 TACCTTATTC CATTTCAGAA ATGTGACCTT CACCGGCTGG AAGAAGGCCC
7951 TCCTGTCACA ACAGTGCTCA CCAGGGAGGA TGGGCTCAAA TACTACAGGA
8001 TGATGCAGAC TGTACGCCGA ATGGAGTTGA AAGCAGATCA GCTGTATAAA
8051 CAGAAAATTA TTCGTGGTTT CTGTCACTTG TGTGATGGTC AGGTGAGTGG
8101 TAGGTTTGTG GTGGAACTGT GTTATTTAGG TACTGAAGTA TGGCTTGTAC
8151 TTATTGGGCT TTACCCTGCC ATATGTATCA GAAGAGTTTG AGGCTGGTAA
8201 TGTAATTTTC TTTTATTTAT TTATTTTTTT GAGACAGTCT CTCTCTGTCG
8251 CCCAGGTTAG AGTACAGTGG TGATCTTGGC TCACTGCAGC CTCTGGTTAG
8301 AGTACAGTGT GATCTTGGCT CACTGCAGCC TCTGTCCACT GGGCTCAAGC
8351 AATCCTCCCA CCTCAGCCTC CCGAGTATGT GGGACCACAG GTGCACACCA
8401 ACACACCCAG CTAATTTTTG TATTTTTGG AGATACGGGG TTTCACTATG
8451 TTGCCCAGGC TAGTCTCAAA CTTCTGGGCT CAAGTGGTCC GCCCACCTTG
8501 GCCTCCCAAG GTGCTAGGAT TACAGGCGTG AGCCACTGTG CCTGGCTGAA
8551 GCCAGTATTT TAGAATTAAA AAGTAGAATG CCAAAACCTG CTATGAAGCT
8601 TAGGCTAAAG AATTCATTCA CACATAACAT TGCCAGTTTT CTGTACCTGT
8651 TCTTAGAGTT TTACTATTTT AAAACTTTCT GGCACTATGA TCGCCTGTAC
8701 TGTATATAAT TTGGAGAGAA AGGATTAGTT TGTTTTTTGT TTTGTGGGCT
8751 TAGGTCAAGG GTTAGAGTCA AATACCTACA AGGGCCAGCC AGGTAGAATA
8801 AATGAGTGAA GAAGGCTAGG TATACAAAAC AGAAAATGGT GACAGGGACT
8851 CATGCTGAAC TGGCACCAGC ATGCCCTACC CAGAGGAATG CCATGACTTG
8901 GTTCCAGCCA GTTGGTGCCA TGTGGAAATC AGGGGTAATG TTTCCTGTTT
8951 TCCATGTCTA AGAGAAGGCG GAAGTCTGGA TTTTCATGTG AAATTCCCAG
9001 TGTTTTAATG TTGACATCTG ATGTAGGCTT TTATTTTAGG TCATCATACA
9051 GGAGAAAGGA AGGAAGTGGC ACATGTGTGG GTTGCCAGTT TATTGCTTCT
9101 GGTTTGGGCC TTCCACTCTG TATTTTGGGG GAAAATAGCT ACTTTCTCTG
9151 GTTATTAATG ACAGGGTCTA CTAGCCCACA TATTTCACTG TGGTCTAGGA
9201 AACGTTTTTA TTTAGAAACA TGTATCATAT TGCCTCATAG TTTCTCCTTC
9251 CTCTAACACA GGAAGCTTGC TGTGTGGGCC TGGAGGCCGG CATCAACCCC
9301 ACAGACCATC TCATCACAGC CTACCGGGCT CACGGCTTTA CTTTCACCCG
9351 GGGCCTTTCC GTCCGAGAAA TTCTCGCAGA GCTTACAGGT TTGCTGTTGA
9401 TTTACAGAAA GGGGAAATGA GTGGATTAAG TTTTTAAATA TCTGTGCATT
```

FIGURE 3, page 3 of 11

```
 9451 AAGATGCTAT TATGAGTTAA TATTTGTTAA AAATTTTAAG TTTCTTTTTT
 9501 TAACCCTCTC TCCTTTGGTG CTCTGGTACT TCTGTTGTGC TCTTGAGTTA
 9551 ACTGACCATT TGTGAAGTTC TCTGGCCCCT CAGGTAAAAG TTTAAAACAG
 9601 GTTGGTGCTA TAAAATCACA GTAGGTTTGG TTATCATTCA AGCATGCCAG
 9651 AAGAAGTCTA GCAGTCATAG AAAGTAAGTT CGGTTGAAGC ACTCCATGGT
 9701 ATGCAATGTA AATTCTAGAA ATCTTCTTAA TATTCCCCTT TTCTTTGTCC
 9751 CCCGTGACTA TTTGTTTGTT TTGGTGGTTT TTTTTTTTT TTTTTTTTGA
 9801 GACTGTGTCT CACTCCGTTG TCCAGGTGG GTGCAGTGGT GTGATCAGGG
 9851 CTCACTGCAA CCTCCACCTC CCGGGTTCAA GTGATTCTCA TGCCTCCACC
 9901 TCCTGAGTAG CTGGGACTAC AGGCATGCAC CACCACACCT GGCTAATTTT
 9951 TGTATTTTTA GTAGAGATGG GGTTTCAACA TGTTGGCCAG GCTGGTCTCC
10001 AACTCCTGAC CTCAGGTGAT CCACCTGCCT TGGCCTCCCA AAGTGTGCTG
10051 GGGTTACAGG CGTGAGCCAC CGCACCTGGC CTGTTTTGTT TTTTTGAGAC
10101 AGAGTCTCGC TTTGTTGCCC AGGCTGGAGT GCAGTGGCCT GCCTCAGCCT
10151 CCCAAAATGC TAGGATTACA GGCGTGAGCC ACTGTGCCCG GTCCTCCTCC
10201 TCCTCCTTTT TTTTTTTTT TTTGAGACA GAGTTTCACT CTTTCACCCA
10251 GGCTGGAGTG GCTGGAGTGA AGTGGTATGA TTTTGGCTCA CTGCAGCCTC
10301 CGCCCCCCGG GTTCAAGCAA TTCTCCTGCC TCAGCCTCCT GAGTAGCTAG
10351 GATTATAGGT GCCCAACCAC CACACCTGGC TAATTTCTGT ATTTTTAGTA
10401 GAGACCAGGT TTCACCATGT TGGCCAGGCT GGTCTTGAAC TCTTGACCTC
10451 AGGTGATCCA CCCTCTTCGG CCTCCCAAAA TGTTAGGATT ACAGGCGTGA
10501 GCCGCCGTGC CCGGCCCTCC TTGACTCTTG AACTATGGTT GTCCCTCTAT
10551 ATATCCAGGG GATTGGTTCT AGGACCCTCG AGTATACAAA AATCCTCAAA
10601 TACTCAAGTC CCAAAGTCAG CCTTCCATAT CTTCGGGTTT GCATCCTGAG
10651 AATATTCTAT TTTCAATACA TGTGTGGCTG AAAAAAAATC TGTGTATAAG
10701 TGTACCTGTG CAGTTCAAAC CCTGTTCAAG GATTGAATAT ATTTAGTGTA
10751 CTAGTATAGG AGAGGTCCTA AGATGTTTGT AACTGGCCAG AAAACCCAGA
10801 AAAGTCCAGG GTATCATCTG GATGGAACAT CTGAAGGAAA CTAAGTGACT
10851 AGAGAGTAGG AAAAGCTGGA AAGGTTGAAG CACATGGAAC TAGTGAAAGG
10901 ACAAGGAGAA ACATGTGTTT GCCTGGAGGG ACAGGTACTT AGACGACTGA
10951 ACTGGCCTCT GTGTTCTAAT GGTTGAGCCT CAGAGTACAT ATTTGGGGTG
11001 CGGTTTGGTT TGCTTTGTAG AGTTGGTTTG TTCTGCACAT GTGTATGTTC
11051 TGCCATTTCC AGGACGAAAA GGAGGTTGTG CTAAAGGGAA AGGAGGATCG
11101 ATGCACATGT ATGCCAAGAA CTTCTACGGG GGCAATGGCA TCGTGGGAGC
11151 GCAGGTAGTC AAGGACGAGG ATTGTGTGCT GCTTTAGATT TGGCCCTGGA
11201 CTTTGTCTTG AAAAACCTTT CACAGCCCCA GACAACTTTT CCTGAAGCTA
11251 GTACAGCCAT GTGCTGCACA GTGACGCTTT GGTCAATGTC GCATATATGA
11301 TGTTGGACCC ATAAGATTAT AATGGAGCTG AAAAATTCCT GTCGCCTAGT
11351 GATGTTGTAG TGGCACAACA CATTACCTTT TCTACGTTTA GGTACACAAA
11401 TATTTGCCT ACAGGATTCA GTAGAGTCAC ATGCTGTGCA GGGTTGTAGC
11451 CTAGGAGCAG TAGGCTCTAC TATACAGCCT AGGTGTGCAG TGGGCTGTAC
11501 CATCTAGGTT CGTGCATTAC AGTATGGTGT TCACATGACA AAATCGCCTA
11551 GTGATGCAAT TCTGAGAATA TATCCCTGTT GTAAGTGAC GCGTGACTAT
11601 TTTGGGGGCT TGGTTTGCTT TTAAAGACCT AGTGCTTCAT ATCCTACCGT
11651 TTGAGAGATG AGTAGATTTG GATGGTGATT TATAATGTTT CCTTTTAGGT
11701 GTCTGCTGTT TTATAAGTAA GCAGGAACCT CTAGCAGTGG AGCCATACCT
11751 TCCCCTTCCT ATTTATATTT CAGTACATTA ATTGCTTTAT CTTGTCAACT
11801 TCATTTTGGG GTCCTTGTTC TCATCAGTTA GTGAATGATG AAGAATTAAC
11851 AGCACAAAAT TATATCCGGA CTGTTTCTTT TCCTTTCTAA TATATTAAGA
11901 TTCTATTATG TGTTGTTTTT TTTTAAACCT AGGTTTTATT TTTCCTTTTG
11951 AAATGGAGTC TTGCTCAGCC GCCCAGGCTG GAGCAGTGGT GTAATCTCAG
12001 CTCACTGCAA CCTCCACCCC CGGGTTCAAG CAATTCTCCT GCCTCAGCCT
12051 CCCGAGTAGC TGGGAATATA GTTACGTGCC ACCATGCCCA ACCATTTTTT
12101 GTATTTTTAG TAGAGACGGG GTTTCACCAT CTTGTCCAGG ATGGTCTCGA
12151 TCTGTGGACC TCGTGATCTG CCCAAAGTGC TGGGATTACA GGCGTGAGCC
12201 ACCACGCCCG GCCAGGTTTT ATTTTTTAAC TCTTGAATGC AGAAATGTTA
12251 GTGCTTACTG GTTAAAATAG AACATAGTAT TTATATATTA CTTTAGTGCT
12301 TTATTGAAAA TATCGGAGGT GGGATAAACA GAGAGATAGG GTTGGAAGGA
12351 GAGTTTGTAG CAGCAGTGTA ATTTCTGTGT CAGATTCTGG CCAGGAGTGA
12401 AAATGCAGGG CATTAATTAG TATCTCCCCT CATGGATTTC TGTGGTTCCT
12451 TTCTCGGTTG TCCTTAATGT TAGGTGCCCC TGGGCGCTGG GATTGCTCTA
12501 GCCTGTAAGT ATAATGGAAA AGATGAGGTC TGCCTGACTT TATATGGCGA
12551 TGGTGCTGCT AACCAGGTAA TTATGTCTCT TAACTTCCCA AAAACAGTCT
```

```
12601 TATTTTCAAA GTCTTTAATA TTTACAGTTG AATTTCTAAA GAAGTAGCAT
12651 ATTGCTTATT AGGTGAAATA GCAAGTCCTA TGGCTAGCTC AAATTTGGTT
12701 GACTTATGGC CAGATTAGAG ATTGACCTCT TAGCGTTGTT TCACAAGAGA
12751 CTTACGGGGG CACATTCCTG TGAAGGAGCT CACCTTTGCT CTACATCAGT
12801 GCTTGGCAAA GGCCCTGTGG TAAAGGACCT CCCCACAACC TATTGCAAAA
12851 CAATACAGAC CCATTCTCTT GGATGTCCGG GCTGGCAGTG TCAAATTCGG
12901 ATAATAGCGT CTGAGTCCTA ACTCAGTTTC TATGCTTCTC TTGTTACCGA
12951 GTAATCCCCA GTCTGTGGCC AGCACTCTGT GAAGCCCTGT TCTAGAGGCT
13001 GATTCTTAGG TGCTGGTTCA CTCTGGCTAT CCAGTGGGCC TGATAGATTT
13051 CATATTGATC TTTTTTCCAG TGTGTTCCTT ACTGCTAGCA TGGCCCCAAA
13101 GAAACAAGTA GTAGTTGGTT TGTCACCTTC CTTAGTTGCA AGAGTATGAT
13151 GCCTGCTACT TCTCCTCCAC CACCCACCCC GCTTTCCCTC ACCACCCAAA
13201 GCTCGGTTTT AGAAGAGGAG GCTTTCTGTG CTTTATGAAA GCTTTCTGTG
13251 CCAGGCAGAG CAGCAGCTGT TAGAGATGAT GAAGCCTGGA GAAAGAAGCC
13301 AAATGAAACC CCTTTTCGTA ACTACTTCCA GGGCCAGATA TTCGAAGCTT
13351 ACAACATGGC AGCTTTGTGG AAATTACCTT GTATTTTCAT CTGTGAGAAT
13401 AATCGCTATG GAATGGGAAC GTCTGTTGAG AGAGCGGCAG CCAGCACTGA
13451 TTACTACAAG AGAGGCGATT TCATTCCTGG GCTGAGAGTA AGGACACCTG
13501 TGGTGGGGCC GGGGCCAAGG CCAAGGCCAA GGGTATGTAC CTTGTGCAGA
13551 CCCTTGACGA TCTTAGAAAC ATTGGAGAGT TTCATTCTCA TACAGGAGCA
13601 GGTCATGTGA AAGTAAAATG GTTTGGGGCA GTTGGATTCA TGCTTCGCCC
13651 CTCCCCTGTT TATTACCAGG TGGATGGAAT GGATATCCTG TGCGTCCGAG
13701 AGGCAACAAG GTTTGCTGCC GCCTATNGTA GATCTGNNNN NNNNNNNNNN
13751 NNNNNNNNNN NNNNNNNNNN NNNNNNNNNN NNNNNNNNNN NNNNNNNNNN
13801 NNNNNNNNNN NNNNNNNNNN NNNNNNNNNN NNNNNNNNNN NNNNNNNNNN
13851 NNNNNNNNNN NNNNNNNNNN NNNNNNNNNN NNNNNNNNNN NNNNNNNNNN
13901 NNNNNNNNNN NNNNNNNNNN NNNNNNNNNN NNNNNNNNNN NNNNNNNNNN
13951 NNNNNNNNNN NNNNNNNNNN NNNNNNNNNN NNNNNNNNNN NNNNNNNNNN
14001 NNNNNNNNNN NNNNNNNNNN NNNNNNNNNN NNNNNNNNNN NNNNNNNNNN
14051 NNNNNNNNNN NNNNNNNNNN NNNNNNNNNN NNNNNNNNNN NNNNNNNNNN
14101 NNNNNNNNNN NNNNNNNNNN NNNNNNNNNN NNNNNNNNNN NNNNNNNNNN
14151 NNNNNNNNNN NNNNNNNNNN NNNNNNNNNN NNNNNNNNNN NNNNNNNNNN
14201 NNNNNNNNNN NNNNNNNNNN NNNNNNNNNN NNNNNNNNNN NNNNNNNNNN
14251 NNNNNNNNNN NNNNNNNNNN NNNNNNNNNN NNNNNNNNNN NNNNNNNNNN
14301 NNNNNNNNNN NNNNNNNNNN NNNNNNNNNN NNNNNNNNNN NNNNNNNNNN
14351 NNNNNNNNNN NNNNNNNNNN NNNNNNNNNN NNNNNNNNNN NNNNNNNNNN
14401 NNNNNNNNNN NNNNNNNNNN NNNNNNNNNN NNNNNNNNNN NNNNNNNNNN
14451 NNNNNNNNNN NNNNNNNNNN NNNNNNNNNN NNNNNNNNNN NNNNNNNNNN
14501 NNNNNNNNNN NNNNNNNNNN NNNNNNNNNN NNNNNNNNNN NNNNNNNNNN
14551 NNNNNNNNNN NNNNNNNNNN NNNNNNNNNN NNNNNNNNNN NNNNNNNNNN
14601 NNNNNNNNNN NNNNNNNNNN NNNNNNNNNN NNNNNNNNNN NNNNNNNNNN
14651 NNNNNNNNNN NNNNNNNNNN NNNNNNNNNN NNNNNNNNNN NNNNNNNNNN
14701 NNNNNNNNNN NNNNNNNNNN NNNNNNNNNN NNNNNNNNNN NNNNNNNNNN
14751 NNNNNNNNNN NNNNNNNNNN NNNNNNNNNN NNNNNNNNNN NNNNNNNNNN
14801 NNNNNNNNNN NNNNNNNNNN NNNNNNNNNN NNNNNNNNNN NNNNNNNNNN
14851 NNNNNNNNNN NNNNNNNNNN NNNNNNNNNN NNNNNNNNNN NNNNNNNNNN
14901 NNNNNNNNNN NNNNNNNNNN NNNNNNNNNN NNNNNNNNNN NNNNNNNNNN
14951 NNNNNNNNNN NNNNNNNNNN NNNNNNNNNN NNNNNNNNNN NNNNNNNNNN
15001 NNNNNNNNNN NNNNNNNNNN NNNNNNNNNN NNNNNNNNNN NNNNNNNNNN
15051 NNNNNNNNNN NNNNNNNNNN NNNNNNNNNN NNNNNNNNNN NNNNNNNNNN
15101 NNNNNNNNNN NNNNNNNNNN NNNNNNNNNN NNNNNNNNNN NNNNNNNNNN
15151 NNNNNNNNNN NNNNNNNNNN NNNNNNNNNN NNNNNNNNNN NNNNNNNNNN
15201 NNNNNNNNNN NNNNNNNNNN NNNNNNNNNN NNNNNNNNNN NNNNNNNNNN
15251 NNNNNNNNNN NNNNNNNNNN NNNNNNNNNN NNNNNNNNNN NNNNNNNNNN
15301 NNNNNNNNNN NNNNNNNNNN NNNNNNNNNN NNNNNNNNNN NNNNNNNNNN
15351 NNNNNNNNNN NNNNNNNNNN NNNNNNNNNN NNNNNNNNNN NNNNNNNNNN
15401 NNNNNNNNNN NNNNNNNNNN NNNNNNNNNN NNNNNNNNNN NNNNNNNNNN
15451 NNNNNNNNNN NNNNNNNNNN NNNNNNNNNN NNNNNNNNNN NNNNNNNNNN
15501 NNNNNNNNNN NNNNNNNNNN NNNNNNNNNN NNNNNNNNNN NNNNNNNNNN
15551 NNNNNNNNNN NNNNNNNNNN NNNNNNNNNN NNNNNNNNNN NNNNNNNNNN
15601 NNNNNNNNNN NNNNNNNNNN NNNNNNNNNN NNNNNNNNNN NNNNNNNNNN
15651 NNNNNNNNNN NNNNNNNNNN NNNNNNNNNN NNNNNNNNNN NNNNNNNNNN
15701 NNNNNNNNNN NNNNNNNNNN NNNNNNNNNN NNNNNCCTTT TTAGTGTTAC
```

FIGURE 3, page 5 of 11

```
15751 TTCAGATGAT ATAGGCATAA GATACATTGG TTTTGCTGGC TGTGCTTCTT
15801 TAGGGGGACT TAAGGGAGAA AGGCAAGGCA CATGGATTTC CTGCTTGGCG
15851 CTCTGATGTC TCAAAGTCTA ATTATCACCA CACACACCAT CTCTGCTGTC
15901 CCCACCCATG TAGTATACAG GAGCCCAAAT GGGTGGGACA AGTGACACTT
15951 CTTTAGAACC TTACATCTAA ATCAAAGCAG CAAGCAAAAA CTTGGCCCCT
16001 GTTGTCGGTA ATGCCAGGGA AGCCATGTGA CTCACCAGTG TACGGTTTTC
16051 TAGAAAAGAC AGAAGCAGTT ATTACAGAAT GTTAGGCTGC GTTCTGGTAT
16101 TTTGAAAGTA TAACAACAAC TCTGCCACGC CTATAGTGAC ATAAGCATTG
16151 GTATGCCCCT TTGTTTCAGA AACACACTTC TGTATTTCAC CTCATTGGGA
16201 CAATCCAACC CCATATCATG TTTCATCACG CCGTCCTTGC TCTACTGGAA
16251 CTGCTCTTAC TGATCGATTA CTACTTTTCC CTCCCCATAG TTACCGTACA
16301 CGAGAAGAAA TTCAGGAAGT AAGAAGTAAG AGTGACCCTA TTATGCTTCT
16351 CAAGGACAGG ATGGTGAACA GCAATCTTGC CAGTGTGGAA GAACTAAAGG
16401 TACAGTCACT TGTTCATGGT GGTTTGAAGG TTGGCTTTAA AAGTTGCCAC
16451 CCCTGGGTGG CCACAGAGTT TGTGTGGGTT CCTCCAAGCC CAGAAAGTGA
16501 TGTCCTGGGA CATAAATAGT TCCATAGTTC CAAAGTCCCT TGGGGTGGGG
16551 GCTTTTCCTT TAGTTTCCTC TATTCAAAAT TGTATTACTC TTCAGATTTC
16601 AGATTTTGGT GGACTGTGAA CCACCATCAC AGTGGCAAAG CCCCCACAGT
16651 AGTATGGTTC TTTTTTCCTA AAAGTATACT GTGGATTTTT AATTCATAAA
16701 ATAGATACAC CCTAGAAATC TGTNNNNNNNN NNNNNNNNNN NNNNNNNNNN
16751 NNNNNNNNNN NNNNNNNNNN NNNNNNNNNN NNNNNNNNNN NNNNNNNNNN
16801 NNNNNNNNNN NNNNNNNNNN NNNNNNNNNN NNNNNNNNNN NNNNNNNNNN
16851 NNNNNNNNNN NNNNNNNNNN NNNNNNNNNN NNNNNNNNNN NNNNNNNNNN
16901 NNNNNNNNNN NNNNNNNNNN NNNNNNNNNN NNNNNNNNNN NNNNNNNNNN
16951 NNNNNNNNNN NNNNNNNNNN NNNNNNNNNN NNNNNNNNNN NNNNNNNNNN
17001 NNNNNNNNNN NNNNNNNNNN NNNNNNNNNN NNNNNNNNNN NNNNNNNNNN
17051 NNNNNNNNNN NNNNNNNNNN NNNNNNNNNN NNNNNNNNNN NNNNNNNNNN
17101 NNNNNNNNNN NNNNNNNNNN NNNNNNNNNN NNNNNNNNNN NNNNNNNNNN
17151 NNNNNNNNNN NNNNNNNNNN NNNNNNNNNN NNNNNNNNNN NNNNNNNNNN
17201 NNNNNNNNNN NNNNNNNNNN NNNNNNNNNN NNNNNNNNNN NNNNNNNNNN
17251 NNNNNNNNNN NNNNNNNNNN NNNNNNNNNN NNNNNNNNNN NNNNNNNNNN
17301 NNNNNNNNNN NNNNNNNNNN NNNNNNNNNN NNNNNNNNNN NNNNNNNNNN
17351 NNNNNNNNNN NNNNNNNNNN NNNNNNNNNN NNNNNNNNNN NNNNNNNNNN
17401 NNNNNNNNNN NNNNNNNNNN NNNNNNNNNN NNNNNNNNNN NNNNNNNNNN
17451 NNNNNNNNNN NNNNNNNNNN NNNNNNNNNN NNNNNNNNNN NNNNNNNNNN
17501 NNNNNNNNNN NNNNNNNNNN NNNNNNNNNN NNNNNNNNNN NNNNNNNNNN
17551 NNNNNNNNNN NNNNNNNNNN NNNNNNNNNN NNNNNNNNNN NNNNNNNNNN
17601 NNNNNNNNNN NNNNNNNNNN NNNNNNNNNN NNNNNNNNNN NNNNNNNNNN
17651 NNNNNNNNNN NNNNNNNNNN NNNNNNNNNN NNNNNNNNNN NNNNNNNNNN
17701 NNNNNNNNNN NNNNNNNNNN NNNNNNNNNN NNNNNNNNNN NNNNNNNNNN
17751 NNNNNNNNNN NNNNNNNNNN NNNNNNNNNN NNNNNNNNNN NNNNNNNNNN
17801 NNNNNNNNNN NNNNNNNNNN NNNNNNNNNN NNNNNNNNNN NNNNNNNNNN
17851 NNNNNNNNNN NNNNNNNNNN NNNNNNNNNN NNNNNNNNNN NNNNNNNNNN
17901 NNNNNNNNNN NNNNNNNNNN NNNNNNNNNN NNNNNNNNNN NNNNNNNNNN
17951 NNNNNNNNNN NNNNNNNNNN NNNNNNNNNN NNNNNNNNNN NNNNNNNNNN
18001 NNNNNNNNNN NNNNNNNNNN NNNNNNNNNN NNNNNNNNNN NNNNNNNNNN
18051 NNNNNNNNNN NNNNNNNNNN NNNNNNNNNN NNNNNNNNNN NNNNNNNNNN
18101 NNNNNNNNNN NNNNNNNNNN NNNNNNNNNN NNNNNNNNNN NNNNNNNNNN
18151 NNNNNNNNNN NNNNNNNNNN NNNNNNNNNN NNNNNNNNNN NNNNNNNNNN
18201 NNNNNNNNNN NNNNNNNNNN NNNNNNNNNN NNNNNNNNNN NNNNNNNNNN
18251 NNNNNNNNNN NNNNNNNNNN NNNNNNNNNN NNNNNNNNNN NNNNNNNNNN
18301 NNNNNNNNNN NNNNNNNNNN NNNNNNNNNN NNNNNNNNNN NNNNNNNNNN
18351 NNNNNNNNNN NNNNNNNNNN NNNNNNNNNN NNNNNNNNNN NNNNNNNNNN    (SEQ ID NO:3)
```

FEATURES:
```
Start:    2090
Exon:     2090-2146
Intron:   2147-7386
Exon:     7387-7446
Intron:   7447-7918
Exon:     7919-8092
Intron:   8093-9240
Exon:     9241-9388
```

FIGURE 3, page 6 of 11

```
Intron:    9389-11062
Exon:      11063-11154
Intron:    11155-12473
Exon:      12474-12566
Intron:    12567-13331
Exon:      13332-13487
Intron:    13488-13669
Exon:      13670-13727
Intron:    13728-15920
Exon:      15921-16007
Intron:    16008-16290
Exon:      16291-
```

CHROMOSOME MAP POSITION:
Chromosome X

ALLELIC VARIANTS (SNPs):

| DNA Position | Major | Minor | Domain | Protein Position | Major | Minor |
|---|---|---|---|---|---|---|
| 1785  | G | T   | Beyond ORF(5') |     |   |    |
| 1895  | G | A   | Beyond ORF(5') |     |   |    |
| 2118  | G | C   | Exon           | 10  | R | P  |
| 5144  | T | C   | Intron         |     |   |    |
| 7932  | A | G   | Exon           | 44  | H | R  |
| 8015  | C | T   | Exon           | 72  | R | C  |
| 8063  | C | A   | Exon           | 88  | R | S  |
| 8066  | G | A   | Exon           | 89  | G | S  |
| 9307  | C | G   | Exon           | 120 | H | D  |
| 9349  | C | T   | Exon           | 134 | R | W  |
| 9350  | G | A   | Exon           | 134 | R | Q  |
| 11066 | G | A   | Exon           | 148 | R | Q  |
| 11128 | G | A   | Exon           | 169 | G | R  |
| 11135 | A | G   | Exon           | 171 | N | S  |
| 11143 | G | A   | Exon           | 174 | V | M  |
| 12486 | G | C   | Exon           | 182 | A | P  |
| 12558 | G | A   | Exon           | 206 | A | T  |
| 13376 | T | C A | Exon           | 223 | F | F L|
| 13378 | C | T   | Exon           | 224 | P | L  |
| 16233 | G | C   | Intron         |     |   |    |
| 16354 | G | A   | Exon           | 330 | R | K  |
| 16377 | T | G   | Exon           | 338 | C | G  |

Context:

| DNA Position | |
|---|---|
| 1785 | TCAAGTAGACAGGGCAGAACTGTCCAACTGCTACGTGATCTTTTAAAGACAAAGTTAGTG GCAGACCATTTACAGAAACCAGATGTTCTGTCTTTTGGCTCTGAGCATGCTGCTAATCTT CATCATCTAGTGTACTGAACGAGATGTACTGAACGAGGGCTGCAGAGCTGCAGCACCGGC AGGAGTAGGCGCTCGGTAGGACGGGGCCTGCACAACCTCCCCGGTAGTCAGCAGAGCGGA ATCTAGGAAGGCTCCTTTCCCGCGGCGCCCTGGAGGCGGGGGCCCCACCTTCCCACGCAG [G,T] CGCTATCAAGCCCCGCCTCCTCACCCGCCCGCGGCGTGGCGTCGGAAAGAGCCCTCAGCC CCTCCCTCTCTGGCGCTGATACCCAATGGGCAGCCTCAGGCCTTTAGCGGGGGCGGGGCA CCCCCTGGACGCCGTTCTGGTTGGCCCGCGGCCCGGCGCAGCGCATGACGTTATTACGAC TCTGTCACGCCGCGGTGCGACTGAGGCGTGGCGTCTGCTGGGGCACCTGAAGGAGACTTG GGGGCACCCGCGTCGTGCCTCCTGGGTTGTGAGGAGTCGCCGCTGCCGCCACTGCCTGTG |
| 1895 | TGCTAATCTTCATCATCTAGTGTACTGAACGAGATGTACTGAACGAGGGCTGCAGAGCTG CAGCACCGGCAGGAGTAGGCGCTCGGTAGGACGGGGCCTGCACAACCTCCCCGGTAGTCA GCAGAGCGGAATCTAGGAAGGCTCCTTTCCCGCGGCGCCCTGGAGGCGGGGGCCCCACCT |

FIGURE 3, page 7 of 11

```
        TCCCACGCAGGCGCTATCAAGCCCCGCCTCCTCACCCGCCCGCGGCGTGGCGTCGGAAAG
        AGCCCTCAGCCCCTCCCTCTCTGGCGCTGATACCCAATGGGCAGCCTCAGGCCTTTAGCG
        [G,A]
        GGGCGGGGCACCCCCTGGACGCCGTTCTGGTTGGCCCGCGGCCCGGCGCAGCGCATGACG
        TTATTACGACTCTGTCACGCCGCGGTGCGACTGAGGCGTGGCGTCTGCTGGGGCACCTGA
        AGGAGACTTGGGGGCACCCGCGTCGTGCCTCCTGGGTTGTGAGGAGTCGCCGCTGCCGCC
        ACTGCCTGTGCTTCATGAGGAAGATGCTCGCCGCCGTCTCCCGCGTGCTGTCTGGCGCTT
        CTCAGAAGCCGGTGAGACCTCCCGGGCGGGCCGGGATGGGGCGCGAGTGGGGCTGAGGCG

2118    GGCGTGGCGTCGGAAAGAGCCCTCAGCCCCTCCCTCTCTGGCGCTGATACCCAATGGGCA
        GCCTCAGGCCTTTAGCGGGGGCGGGGCACCCCCTGGACGCCGTTCTGGTTGGCCCGCGGC
        CCGGCGCAGCGCATGACGTTATTACGACTCTGTCACGCCGCGGTGCGACTGAGGCGTGGC
        GTCTGCTGGGGCACCTGAAGGAGACTTGGGGGCACCCGCGTCGTGCCTCCTGGGTTGTGA
        GGAGTCGCCGCTGCCGCCACTGCCTGTGCTTCATGAGGAAGATGCTCGCCGCCGTCTCCC
        [G,C]
        CGTGCTGTCTGGCGCTTCTCAGAAGCCGGTGAGACCTCCCGGGCGGGCCGGGATGGGGCG
        CGAGTGGGGCTGAGGCGGGGCCGGAGGGCAGGGCGGGCCAGGCCGGGCCACCCAGAGCGG
        GGTGGAAGGCGCCAGGGGAGCCGGGGAGCCTTTA

5144    TGAATGCATTTAAAATGTTATTTTATTGTTTGCATTTCTGTATGGCTCCTTTTGTGAGAT
        CTTTACTAGCAATGTTTTGGCTTTATAAGTGGTAGGTAAGAGTTTTAATTTACACTGTTA
        GAATCTGGAATTTTTGAAACGTTTTTCCTCTTTCACATGAATGGTTCCTATGTATTTAGG
        AAGTTAAAGTTTTACTTTTTTTAATTAATTTTTTTTTTAGGCTGGAATGCAGTGGCAC
        AGTCATAGCTCACTGTAGCCTCAGGTGTGTGCCACCATACCTGACTAATTTTTTAATATT
        [T,C]
        ATTTTTGTAGAGATGAGAGTCTCATGTTGCCCAGGCTGGCTTTGAACTCCTGGCTTCAAG
        TGGTCCTCCCACCCTGGCCTCCCAAAGTGCTGGGATTATAGGTGTGAGCCATCATGCCC
        GGCCTAGTTTTTATTTTTAAAATTTGAGTGGGTTGTTCGTGGTCTCTGTCAGAGAGGAA
        TCCCATTTAACAGAGAATCTTTTTATGGCTCTCCAGAGAAAATGAATGGTAAACTTATCT
        TTTCAACAAGCTCTCACTCAGAAATGATACACACACACTTCTGATAGGACTTTTAGCTTC

7932    AAGAGTCTTAGTTGTTTCTTTGAAGGTTCTTTCAACCTATAACTCAGTTGGCTTCTAGGG
        GCTTTCAGTGAAAATCATCTTAGAAAGATTTCCTTCCCCCAAGCCCCATCTCATTGCACA
        GTGAGGTTTATGGATTTAAGGAACAGAGGCGATATGAAGCATTACTGATGTGCTCCTTTG
        CAGTTTTTCAAGTTCAATATTATTTGCAATGGAGTTAGATCTTAGAGTGGTCAACAGTGT
        TTGCAATGTAGTATGTGGAGGATAATAACTACCTTATTCCATTTCAGAAATGTGACCTTC
        [A,G]
        CCGGCTGGAAGAAGGCCCTCCTGTCACAACAGTGCTCACCAGGGAGGATGGGCTCAAATA
        CTACAGGATGATGCAGACTGTACGCCGAATGGAGTTGAAAGCAGATCAGCTGTATAAACA
        GAAAATTATTCGTGGTTTCTGTCACTTGTGTGATGGTCAGGTGAGTGGTAGGTTTGTGGT
        GGAACTGTGTTATTTAGGTACTGAAGTATGGCTTGTACTTATTGGGCTTTACCCTGCCAT
        ATGTATCAGAAGAGTTTGAGGCTGGTAATGTAATTTTCTTTTATTTATTTATTTTTTTGA

8015    AAAGATTTCCTTCCCCCAAGCCCCATCTCATTGCACAGTGAGGTTTATGGATTTAAGGAA
        CAGAGGCGATATGAAGCATTACTGATGTGCTCCTTTGCAGTTTTTCAAGTTCAATATTAT
        TTGCAATGGAGTTAGATCTTAGAGTGGTCAACAGTGTTTGCAATGTAGTATGTGGAGGAT
        AATAACTACCTTATTCCATTTCAGAAATGTGACCTTCACCGGCTGGAAGAAGGCCCTCCT
        GTCACAACAGTGCTCACCAGGGAGGATGGGCTCAAATACTACAGGATGATGCAGACTGTA
        [C,T]
        GCCGAATGGAGTTGAAAGCAGATCAGCTGTATAAACAGAAAATTATTCGTGGTTTCTGTC
        ACTTGTGTGATGGTCAGGTGAGTGGTAGGTTTGTGGTGGAACTGTGTTATTTAGGTACTG
        AAGTATGGCTTGTACTTATTGGGCTTTACCCTGCCATATGTATCAGAAGAGTTTGAGGCT
        GGTAATGTAATTTTCTTTTATTTATTTATTTTTTGAGACAGTCTCTCTCTGTCGCCCAG
        GTTAGAGTACAGTGGTGATCTTGGCTCACTGCAGCCTCTGGTTAGAGTACAGTGTGATCT

8063    GGATTTAAGGAACAGAGGCGATATGAAGCATTACTGATGTGCTCCTTTGCAGTTTTTCAA
        GTTCAATATTATTTGCAATGGAGTTAGATCTTAGAGTGGTCAACAGTGTTTGCAATGTAG
        TATGTGGAGGATAATAACTACCTTATTCCATTTCAGAAATGTGACCTTCACCGGCTGGAA
        GAAGGCCCTCCTGTCACAACAGTGCTCACCAGGGAGGATGGGCTCAAATACTACAGGATG
        ATGCAGACTGTACGCCGAATGGAGTTGAAAGCAGATCAGCTGTATAAACAGAAAATTATT
        [C,A]
        GTGGTTTCTGTCACTTGTGTGATGGTCAGGTGAGTGGTAGGTTTGTGGTGGAACTGTGTT
        ATTTAGGTACTGAAGTATGGCTTGTACTTATTGGGCTTTACCCTGCCATATGTATCAGAA
```

FIGURE 3, page 8 of 11

```
        GAGTTTGAGGCTGGTAATGTAATTTTCTTTTATTTATTTATTTTTTTGAGACAGTCTCTC
        TCTGTCGCCCAGGTTAGAGTACAGTGGTGATCTTGGCTCACTGCAGCCTCTGGTTAGAGT
        ACAGTGTGATCTTGGCTCACTGCAGCCTCTGTCCACTGGGCTCAAGCAATCCTCCCACCT

8066   TTTAAGGAACAGAGGCGATATGAAGCATTACTGATGTGCTCCTTTGCAGTTTTTCAAGTT
        CAATATTATTTGCAATGGAGTTAGATCTTAGAGTGGTCAACAGTGTTTGCAATGTAGTAT
        GTGGAGGATAATAACTACCTTATTCCATTTCAGAAATGTGACCTTCACCGGCTGGAAGAA
        GGCCCTCCTGTCACAACAGTGCTCACCAGGGAGGATGGGCTCAAATACTACAGGATGATG
        CAGACTGTACGCCGAATGGAGTTGAAAGCAGATCAGCTGTATAAACAGAAAATTATTCGT
        [G,A]
        GTTTCTGTCACTTGTGTGATGGTCAGGTGAGTGGTAGGTTTGTGGTGGAACTGTGTTATT
        TAGGTACTGAAGTATGGCTTGTACTTATTGGGCTTTACCCTGCCATATGTATCAGAAGAG
        TTTGAGGCTGGTAATGTAATTTTCTTTTATTTATTTATTTTTTGAGACAGTCTCTCTCT
        GTCGCCCAGGTTAGAGTACAGTGGTGATCTTGGCTCACTGCAGCCTCTGGTTAGAGTACA
        GTGTGATCTTGGCTCACTGCAGCCTCTGTCCACTGGGCTCAAGCAATCCTCCCACCTCAG

9307   AATGTTGACATCTGATGTAGGCTTTTATTTTAGGTCATCATACAGGAGAAAGGAAGGAAG
        TGGCACATGTGTGGGTTGCCAGTTTATTGCTTCTGGTTTGGGCCTTCCACTCTGTATTTT
        GGGGGAAAATAGCTACTTTCTCTGGTTATTAATGACAGGGTCTACTAGCCCACATATTTC
        ACTGTGGTCTAGGAAACGTTTTTATTTAGAAACATGTATCATATTGCCTCATAGTTTCTC
        CTTCCTCTAACACAGGAAGCTTGCTGTGTGGGCCTGGAGGCCGGCATCAACCCCACAGAC
        [C,G]
        ATCTCATCACAGCCTACCGGGCTCACGGCTTTACTTTCACCCGGGGCCTTTCCGTCCGAG
        AAATTCTCGCAGAGCTTACAGGTTTGCTGTTGATTTACAGAAAGGGGAAATGAGTGGATT
        AAGTTTTTAAATATCTGTGCATTAAGATGCTATTATGAGTTAATATTTGTTAAAAATTTT
        AAGTTTCTTTTTTTAACCCTCTCTCCTTTGGTGCTCTGGTACTTCTGTTGTGCTCTTGAG
        TTAACTGACCATTTGTGAAGTTCTCTGGCCCCTCAGGTAAAAGTTTAAAACAGGTTGGTG

9349   CAGGAGAAAGGAAGGAAGTGGCACATGTGTGGGTTGCCAGTTTATTGCTTCTGGTTTGGG
        CCTTCCACTCTGTATTTTGGGGGAAAATAGCTACTTTCTCTGGTTATTAATGACAGGGTC
        TACTAGCCCACATATTTCACTGTGGTCTAGGAAACGTTTTTATTTAGAAACATGTATCAT
        ATTGCCTCATAGTTTCTCCTTCCTCTAACACAGGAAGCTTGCTGTGTGGGCCTGGAGGCC
        GGCATCAACCCCACAGACCATCTCATCACAGCCTACCGGGCTCACGGCTTTACTTTCACC
        [C,T]
        GGGGCCTTTCCGTCCGAGAAATTCTCGCAGAGCTTACAGGTTTGCTGTTGATTTACAGAA
        AGGGGAAATGAGTGGATTAAGTTTTTAAATATCTGTGCATTAAGATGCTATTATGAGTTA
        ATATTTGTTAAAAATTTTAAGTTTCTTTTTTTAACCCTCTCTCCTTTGGTGCTCTGGTAC
        TTCTGTTGTGCTCTTGAGTTAACTGACCATTTGTGAAGTTCTCTGGCCCCTCAGGTAAAA
        GTTTAAAACAGGTTGGTGCTATAAAATCACAGTAGGTTTGGTTATCATTCAAGCATGCCA

9350   AGGAGAAAGGAAGGAAGTGGCACATGTGTGGGTTGCCAGTTTATTGCTTCTGGTTTGGGC
        CTTCCACTCTGTATTTTGGGGGAAAATAGCTACTTTCTCTGGTTATTAATGACAGGGTCT
        ACTAGCCCACATATTTCACTGTGGTCTAGGAAACGTTTTTATTTAGAAACATGTATCATA
        TTGCCTCATAGTTTCTCCTTCCTCTAACACAGGAAGCTTGCTGTGTGGGCCTGGAGGCCG
        GCATCAACCCCACAGACCATCTCATCACAGCCTACCGGGCTCACGGCTTTACTTTCACCC
        [G,A]
        GGGCCTTTCCGTCCGAGAAATTCTCGCAGAGCTTACAGGTTTGCTGTTGATTTACAGAAA
        GGGGAAATGAGTGGATTAAGTTTTTAAATATCTGTGCATTAAGATGCTATTATGAGTTAA
        TATTTGTTAAAAATTTTAAGTTTCTTTTTTTAACCCTCTCTCCTTTGGTGCTCTGGTACT
        TCTGTTGTGCTCTTGAGTTAACTGACCATTTGTGAAGTTCTCTGGCCCCTCAGGTAAAAG
        TTTAAAACAGGTTGGTGCTATAAAATCACAGTAGGTTTGGTTATCATTCAAGCATGCCAG

11066   TCCTAAGATGTTTGTAACTGGCCAGAAAACCCAGAAAAGTCCAGGGTATCATCTGGATGG
        AACATCTGAAGGAAACTAAGTGACTAGAGAGTAGGAAAAGCTGGAAAGGTTGAAGCACAT
        GGAACTAGTGAAAGGACAAGGAGAAACATGTGTTTGCCTGGAGGGACAGGTACTTAGACG
        ACTGAACTGGCCTCTGTGTTCTAATGGTTGAGCCTCAGAGTACATATTTGGGGTGCGGTT
        TGGTTTGCTTTGTAGAGTTGGTTTGTTCTGCACATGTGTATGTTCTGCCATTTCCAGGAC
        [G,A]
        AAAAGGAGGTTGTGCTAAAGGGAAAGGAGGATCGATGCACATGTATGCCAAGAACTTCTA
        CGGGGGCAATGGCATCGTGGGAGCGCAGGTAGTCAAGGACGAGGATTGTGTGCTGCTTTA
        GATTTGGCCCTGGACTTTGTCTTGAAAAACCTTTCACAGCCCAGACAACTTTTCCTGAA
        GCTAGTACAGCCATGTGCTGCACAGTGACGCTTTGGTCAATGTCGCATATATGATGTTGG
        ACCCATAAGATTATAATGGAGCTGAAAAATTCCTGTCGCCTAGTGATGTTGTAGTGGCAC
```

FIGURE 3, page 9 of 11

11128   CATCTGAAGGAAACTAAGTGACTAGAGAGTAGGAAAAGCTGGAAAGGTTGAAGCACATGG
        AACTAGTGAAAGGACAAGGAGAAACATGTGTTTGCCTGGAGGGACAGGTACTTAGACGAC
        TGAACTGGCCTCTGTGTTCTAATGGTTGAGCCTCAGAGTACATATTTGGGGTGCGGTTTG
        GTTTGCTTTGTAGAGTTGGTTTGTTCTGCACATGTGTATGTTCTGCCATTTCCAGGACGA
        AAAGGAGGTTGTGCTAAAGGGAAAGGAGGATCGATGCACATGTATGCCAAGAACTTCTAC
        [G,A]
        GGGGCAATGGCATCGTGGGAGCGCAGGTAGTCAAGGACGAGGATTGTGTGCTGCTTTAGA
        TTTGGCCCTGGACTTTGTCTTGAAAAACCTTTCACAGCCCCAGACAACTTTTCCTGAAGC
        TAGTACAGCCATGTGCTGCACAGTGACGCTTTGGTCAATGTCGCATATATGATGTTGGAC
        CCATAAGATTATAATGGAGCTGAAAAATTCCTGTCGCCTAGTGATGTTGTAGTGGCACAA
        CACATTACCTTTTCTACGTTTAGGTACACAAATATTTTGCCTACAGGATTCAGTAGAGTC

11135   AGGAAACTAAGTGACTAGAGAGTAGGAAAAGCTGGAAAGGTTGAAGCACATGGAACTAGT
        GAAAGGACAAGGAGAAACATGTGTTTGCCTGGAGGGACAGGTACTTAGACGACTGAACTG
        GCCTCTGTGTTCTAATGGTTGAGCCTCAGAGTACATATTTGGGGTGCGGTTTGGTTTGCT
        TTGTAGAGTTGGTTTGTTCTGCACATGTGTATGTTCTGCCATTTCCAGGACGAAAAGGAG
        GTTGTGCTAAAGGGAAAGGAGGATCGATGCACATGTATGCCAAGAACTTCTACGGGGGCA
        [A,G]
        TGGCATCGTGGGAGCGCAGGTAGTCAAGGACGAGGATTGTGTGCTGCTTTAGATTTGGCC
        CTGGACTTTGTCTTGAAAAACCTTTCACAGCCCCAGACAACTTTTCCTGAAGCTAGTACA
        GCCATGTGCTGCACAGTGACGCTTTGGTCAATGTCGCATATATGATGTTGGACCCATAAG
        ATTATAATGGAGCTGAAAAATTCCTGTCGCCTAGTGATGTTGTAGTGGCACAACACATTA
        CCTTTTCTACGTTTAGGTACACAAATATTTTGCCTACAGGATTCAGTAGAGTCACATGCT

11143   AAGTGACTAGAGAGTAGGAAAAGCTGGAAAGGTTGAAGCACATGGAACTAGTGAAAGGAC
        AAGGAGAAACATGTGTTTGCCTGGAGGGACAGGTACTTAGACGACTGAACTGGCCTCTGT
        GTTCTAATGGTTGAGCCTCAGAGTACATATTTGGGGTGCGGTTTGGTTTGCTTTGTAGAG
        TTGGTTTGTTCTGCACATGTGTATGTTCTGCCATTTCCAGGACGAAAAGGAGGTTGTGCT
        AAAGGGAAAGGAGGATCGATGCACATGTATGCCAAGAACTTCTACGGGGGCAATGGCATC
        [G,A]
        TGGGAGCGCAGGTAGTCAAGGACGAGGATTGTGTGCTGCTTTAGATTTGGCCCTGGACTT
        TGTCTTGAAAAACCTTTCACAGCCCCAGACAACTTTTCCTGAAGCTAGTACAGCCATGTG
        CTGCACAGTGACGCTTTGGTCAATGTCGCATATATGATGTTGGACCCATAAGATTATAAT
        GGAGCTGAAAAATTCCTGTCGCCTAGTGATGTTGTAGTGGCACAACACATTACCTTTTCT
        ACGTTTAGGTACACAAATATTTTGCCTACAGGATTCAGTAGAGTCACATGCTGTGCAGGG

12486   TTACAGGCGTGAGCCACCACGCCCGGCCAGGTTTTATTTTTTAACTCTTGAATGCAGAAA
        TGTTAGTGCTTACTGGTTAAAATAGAACATAGTATTTATATATTACTTTAGTGCTTTATT
        GAAAATATCGGAGGTGGGATAAACAGAGAGATAGGGTTGGAAGGAGAGTTTGTAGCAGCA
        GTGTAATTTCTGTGTCAGATTCTGGCCAGGAGTGAAAATGCAGGGCATTAATTAGTATCT
        CCCCTCATGGATTTCTGTGGTTCCTTTCTCGGTTGTCCTTAATGTTAGGTGCCCCTGGGC
        [G,C]
        CTGGGATTGCTCTAGCCTGTAAGTATAATGGAAAAGATGAGGTCTGCCTGACTTTATATG
        GCGATGGTGCTGCTAACCAGGTAATTATGTCTCTTAACTTCCCAAAAACAGTCTTATTTT
        CAAAGTCTTTAATATTTACAGTTGAATTTCTAAAGAAGTAGCATATTGCTTATTAGGTGA
        AATAGCAAGTCCTATGGCTAGCTCAAATTTGGTTGACTTATGGCCAGATTAGAGATTGAC
        CTCTTAGCGTTGTTTCACAAGAGACTTACGGGGGCACATTCCTGTGAAGGAGCTCACCTT

12558   CTGGTTAAAATAGAACATAGTATTTATATATTACTTTAGTGCTTTATTGAAAATATCGGA
        GGTGGGATAAACAGAGAGATAGGGTTGGAAGGAGAGTTTGTAGCAGCAGTGTAATTTCTG
        TGTCAGATTCTGGCCAGGAGTGAAAATGCAGGGCATTAATTAGTATCTCCCCTCATGGAT
        TTCTGTGGTTCCTTTCTCGGTTGTCCTTAATGTTAGGTGCCCCTGGGCGCTGGGATTGCT
        CTAGCCTGTAAGTATAATGGAAAAGATGAGGTCTGCCTGACTTTATATGGCGATGGTGCT
        [G,A]
        CTAACCAGGTAATTATGTCTCTTAACTTCCCAAAAACAGTCTTATTTTCAAAGTCTTTAA
        TATTTACAGTTGAATTTCTAAAGAAGTAGCATATTGCTTATTAGGTGAAATAGCAAGTCC
        TATGGCTAGCTCAAATTTGGTTGACTTATGGCCAGATTAGAGATTGACCTCTTAGCGTTG
        TTTCACAAGAGACTTACGGGGGCACATTCCTGTGAAGGAGCTCACCTTTGCTCTACATCA
        GTGCTTGGCAAAGGCCCTGTGGTAAAGGACCTCCCCACAACCTATTGCAAAACAATACAG

13376   TCCTTACTGCTAGCATGGCCCCAAAGAAACAAGTAGTAGTTGGTTTGTCACCTTCCTTAG
        TTGCAAGAGTATGATGCCTGCTACTTCTCCTCCACCACCCACCCCGCTTTCCCTCACCAC

FIGURE 3, page 10 of 11

```
         CCAAAGCTCGGTTTTAGAAGAGGAGGCTTTCTGTGCTTTATGAAAGCTTTCTGTGCCAGG
         CAGAGCAGCAGCTGTTAGAGATGATGAAGCCTGGAGAAAGAAGCCAAATGAAACCCCTTT
         TCGTAACTACTTCCAGGGCCAGATATTCGAAGCTTACAACATGGCAGCTTTGTGGAAATT
         [T,C,A]
         CCTTGTATTTTCATCTGTGAGAATAATCGCTATGGAATGGGAACGTCTGTT

13378    CTTACTGCTAGCATGGCCCCAAAGAAACAAGTAGTAGTTGGTTTGTCACCTTCCTTAGTT
         GCAAGAGTATGATGCCTGCTACTTCTCCTCCACCACCCACCCCGCTTTCCCTCACCACCC
         AAAGCTCGGTTTTAGAAGAGGAGGCTTTCTGTGCTTTATGAAAGCTTTCTGTGCCAGGCA
         GAGCAGCAGCTGTTAGAGATGATGAAGCCTGGAGAAAGAAGCCAAATGAAACCCCTTTTC
         GTAACTACTTCCAGGGCCAGATATTCGAAGCTTACAACATGGCAGCTTTGTGGAAATTAC
         [C,T]
         TTGTATTTTCATCTGTGAGAATAATCGCTATGGAATGGGAA

16233    GTGGGACAAGTGACACTTCTTTAGAACCTTACATCTAAATCAAAGCAGCAAGCAAAAACT
         TGGCCCCTGTTGTCGGTAATGCCAGGGAAGCCATGTGACTCACCAGTGTACGGTTTTCTA
         GAAAAGACAGAAGCAGTTATTACAGAATGTGCGTTCTGGTATTTTGAAAGTATA
         ACAACAACTCTGCCACGCCTATAGTGACATAAGCATTGGTATGCCCCTTTGTTTCAGAAA
         CACACTTCTGTATTTCACCTCATTGGGACAATCCAACCCCATATCATGTTTCATCACGCC
         [G,C]
         TCCTTGCTCTACTGGAACTGCTCTTACTGATCGATTACTACTTTTCCCTCCCCATAGTTA
         CCGTACACGAGAAGAAATTCAGGAAGTAAGAAGTAAGAGTGACCCTATTATGCTTCTCAA
         GGACAGGATGGTGAACAGCAATCTTGCCAGTGTGGAAGAACTAAAGGTACAGTCACTTGT
         TCATGGTGGTTTGAAGGTTGGCTTTAAAAGTTGCCACCCCTGGGTGGCCACAGAGTTTGT
         GTGGGTTCCTCCAAGCCCAGAAAGTGATGTCCTGGGACATAAATAGTTCCATAGTTCCAA

16354    AAAAGACAGAAGCAGTTATTACAGAATGTTAGGCTGCGTTCTGGTATTTTGAAAGTATAA
         CAACAACTCTGCCACGCCTATAGTGACATAAGCATTGGTATGCCCCTTTGTTTCAGAAAC
         ACACTTCTGTATTTCACCTCATTGGGACAATCCAACCCCATATCATGTTTCATCACGCCG
         TCCTTGCTCTACTGGAACTGCTCTTACTGATCGATTACTACTTTTCCCTCCCCATAGTTA
         CCGTACACGAGAAGAAATTCAGGAAGTAAGAAGTAAGAGTGACCCTATTATGCTTCTCAA
         [G,A]
         GACAGGATGGTGAACAGCAATCTTGCCAGTGTGGAAGAACTAAAGGTACAGTCACTTGTT
         CATGGTGGTTTGAAGGTTGGCTTTAAAAGTTGCCACCCCTGGGTGGCCACAGAGTTTGTG
         TGGGTTCCTCCAAGCCCAGAAAGTGATGTCCTGGGACATAAATAGTTCCATAGTTCCAAA
         GTCCCTTGGGGTGGGGGCTTTTCCTTTAGTTTCCTCTATTCAAAATTGTATTACTCTTCA
         GATTTCAGATTTTGGTGGACTGTGAACCACCATCACAGTGGCAAAGCCCCCACAGTAGTA

16377    GAATGTTAGGCTGCGTTCTGGTATTTTGAAAGTATAACAACAACTCTGCCACGCCTATAG
         TGACATAAGCATTGGTATGCCCCTTTGTTTCAGAAACACACTTCTGTATTTCACCTCATT
         GGGACAATCCAACCCCATATCATGTTTCATCACGCCGTCCTTGCTCTACTGGAACTGCTC
         TTACTGATCGATTACTACTTTTCCCTCCCCATAGTTACCGTACACGAGAAGAAATTCAGG
         AAGTAAGAAGTAAGAGTGACCCTATTATGCTTCTCAAGGACAGGATGGTGAACAGCAATC
         [T,G]
         TGCCAGTGTGGAAGAACTAAAGGTACAGTCACTTGTTCATGGTGGTTTGAAGGTTGGCTT
         TAAAAGTTGCCACCCCTGGGTGGCCACAGAGTTTGTGTGGGTTCCTCCAAGCCCAGAAAG
         TGATGTCCTGGGACATAAATAGTTCCATAGTTCCAAAGTCCCTTGGGGTGGGGGCTTTTC
         CTTTAGTTTCCTCTATTCAAAATTGTATTACTCTTCAGATTTCAGATTTTGGTGGACTGT
         GAACCACCATCACAGTGGCAAAGCCCCCACAGTAGTATGGTTCTTTTTTCCTAAAAGTAT
```

FIGURE 3, page 11 of 11

ISOLATED NUCLEIC ACID MOLECULES ENCODING HUMAN PYRUVATE DEHYDROGENASE E1-ALPHA SUBUNIT PROTEINS

The present application is a continuation-in-part of U.S. Ser. No. 09/799,344, filed Mar. 6, 2000 now abandoned.

FIELD OF THE INVENTION

The present invention is in the field of enzyme proteins that are related to the pyruvate dehydrogenase enzyme subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the pyruvate dehydrogenase subfamily.

Pyruvate Dehydrogenase Complex, E1 Subunit

The novel human protein, and encoding gene, provided by the present invention is related to the pyruvate dehydrogenase E1-alpha precursor protein (see De Meirleir et al., *J. Biol. Chem.* 263 (4), 1991–1995 (1988)). The pyruvate dehydrogenase (PDH) complex is comprised of a plurality of each of three different enzymes: pyruvate decarboxylase (E1), dihydrolipoyl transacetylase (E2), and dihydrolipoyl dehydrogenase (E3). Each of these three different enzymes is comprised of multiple subunits; the E1 enzyme is a heterotetramer consisting of two alpha and two beta subunits. The E1-alpha subunit contains the E1 active site and is therefore critical for the functioning of the PDH complex. PDH plays an important role in all metabolically active tissues; however, it plays a particularly critical role in the brain since the brain normally obtains all its energy from aerobic oxidation of glucose.

Genetic defects in the PDH complex are the main cause of lactic acidosis, particularly in children. Furthermore, in the majority of cases, the specific genetic defects leading to lactic acidosis are in the E1-alpha subunit. PDH deficiency due to genetic defects can cause fatal lactic acidosis in newborns and chronic neurological dysfunction and neurodegeneration with gross structural abnormalities in the CNS. PDH deficiency is one of the most common pathologies of mitochondrial energy metabolism. It is common for even heterozygous females to show severe clinical symptoms.

For a further review of the PDH complex, particularly PDH-E 1 and the PDH-E1-alpha subunit, see:

1. Bindoff, L. A.; Birch-Machin, M. A.; Farnsworth, L.; Gardner-Medwin, D.; Lindsay, J. G.; Turnbull, D. M. Familial intermittent ataxia due to a defect of the E1 component of pyruvate dehydrogenase complex. J. Neurol. Sci. 93: 311–318, 1989. PubMed ID: 2592988;
2. Blair, H. J.; Reed, V.; Laval, S. H.; Boyd, Y. The locus for pyruvate dehydrogenase E1 alpha-subunit (Pdha1) lies between Plp and Amg on the mouse X chromosome. Mammalian Genome 4: 230–233, 1993. PubMed ID: 7684627;
3. Borglum, A. D.; Flint, T.; Hansen, L. L.; Kruse, T. A. Refined localization of the pyruvate dehydrogenase E1-alpha gene (PDHA1) by linkage analysis. Hum. Genet. 99: 80–82, 1997. PubMed ID: 9003499;
4. Brown, G. K.; Haan, E. A.; Kirby, D. M.; Scholem, R. D.; Wraith, J. E.; Rogers, J. G.; Danks, D. M. 'Cerebral' lactic acidosis: defects in pyruvate metabolism with profound brain damage and minimal systemic acidosis. Europ. J. Pediat. 147: 10–14, 1988. PubMed ID: 3123240;
5. Brown, G. K.; Otero, L. J.; LeGris, M.; Brown, R. M. Pyruvate dehydrogenase deficiency. J. Med. Genet. 31: 875–879, 1994. PubMed ID: 7853374;
6. Brown, R. M.; Dahl, H.-H. M.; Brown, G. K. An homologous locus to the human X-linked pyruvate dehydrogenase E1-alpha subunit gene is located at the distal end of the mouse X chromosome. (Abstract) Cytogenet. Cell Genet. 51: 970, 1989.;
7. Brown, R. M.; Dahl, H.-H. M.; Brown, G. K. X-chromosome localization of the functional gene for the E1-alpha subunit of the human pyruvate dehydrogenase complex. Genomics 4: 174–181, 1989. PubMed ID: 2737678;
8. Brown, R. M.; Dahl, H.-H. M.; Brown, G. K. Regional localization of the X-linked human pyruvate dehydrogenase E1-alpha subunit gene. (Abstract) Cytogenet. Cell Genet. 51: 970, 1989.;
9. Brown, R. M.; Otero, L. J.; Brown, G. K. Transfection screening for primary defects in the pyruvate dehydrogenase E1-alpha subunit gene. Hum. Molec. Genet. 6: 1361–1367, 1997. PubMed ID: 9259285;
10. Chun, K.; MacKay, N.; Petrova-Benedict, R.; Robinson, B. H. Mutations in the X-linked E1-alpha subunit of pyruvate dehydrogenase leading to deficiency of the pyruvate dehydrogenase complex. Hum. Molec. Genet. 2: 449–454, 1993. PubMed ID: 8504306;
11. Chun, K.; MacKay, N.; Petrova-Benedict, R.; Robinson, B. H. Pyruvate dehydrogenase deficiency due to a 20-bp deletion in exon 11 of the pyruvate dehydrogenase (PDH) E1-alpha gene. Am. J. Hum. Genet. 49: 414–420, 1991. PubMed ID: 1907799;
12. Dahl, H.-H. M. Pyruvate dehydrogenase E1-alpha deficiency: males and females differ yet again. Am. J. Hum. Genet. 56: 553–557, 1995. PubMed ID: 7887408;
13. Dahl, H.-H. M.; Brown, G. K. Pyruvate dehydrogenase deficiency in a male caused by a point mutation (F205L) in the E1-alpha subunit. Hum. Mutat. 3: 152–155, 1994. PubMed ID: 8199595;
14. Dahl, H.-H. M.; Brown, G. K.; Brown, R. M.; Hansen, L. L.; Kerr, D. S.; Wexler, I. D.; Patel, M. S.; De Meirleir, L.; Lissens, W.; Chun, K.; MacKay, N.; Robinson, B. H. Mutations and polymorphisms in the pyruvate dehydrogenase E1-alpha gene. Hum. Mutat. 1: 97–102, 1992. PubMed ID: 1301207;
15. Dahl, H.-H. M.; Hansen, L. L.; Brown, R. M.; Danks, D. M.; Rogers, J. G.; Brown, G. K. X-linked pyruvate dehydrogenase E1-alpha subunit deficiency in heterozygous females: variable manifestation of the same mutation. J. Inherit. Metab. Dis. 15: 835–847, 1992. PubMed ID: 1293379;
16. Dahl, H.-H. M.; Maragos, C.; Brown, R. M.; Hansen, L. L.; Brown, G. K. Pyruvate dehydrogenase deficiency caused by deletion of a 7-bp repeat sequence in the E1-alpha gene. Am. J. Hum. Genet. 47: 286–293, 1990. PubMed ID: 2378353;
17. de Meirleir, L.; Lissens, W.; Vamos, E.;

Liebaers, I. Pyruvate dehydrogenase (PDH) deficiency caused by a 21-base pair insertion mutation in the E1-alpha subunit. Hum. Genet. 88: 649–652, 1992. PubMed ID: 1551669; 18. De Meirleir, L.; Specola, N.; Seneca, S.; Lissens, W. Pyruvate dehydrogenase E1-alpha deficiency in a family: different clinical presentation in two siblings. J. Inherit. Metab. Dis. 21: 224–226, 1998. PubMed ID: 9686362; 19. de Meirleir, L. J.; Lissens, W.; Vamos, E.; Liebaers, I.; Pyruvate dehydrogenase deficiency due to a mutation of the E1-alpha subunit. J. Inherit. Metab. Dis. 14: 301–304, 1991. PubMed ID: 1770778; 20. Endo, H.; Hasegawa, K.; Narisawa, K.; Tada, K.; Kagawa, Y.; Ohta, S. Defective gene in lactic acidosis: abnormal pyruvate dehydrogenase E1 alpha-subunit caused by a frame shift. Am. J. Hum. Genet. 44: 358–364, 1989. PubMed ID: 2537010; 21. Endo, H.; Miyabayashi, S.; Tada, K.; Narisawa, K. A four-nucleotide insertion at the E1-alpha gene in a patient with pyruvate dehydrogenase deficiency. J. Inherit. Metab. Dis. 14: 793–799, 1991. PubMed ID: 1779625; 22. Fitzgerald, J.; Wilcox, S. A.; Graves, J. A. M.; Dahl, H.-H. M. A eutherian X-linked gene, PDHA1, is autosomal in marsupials: a model for the evolution of a second, testis-specific variant in eutherian mammals. Genomics 18: 636–642, 1993. PubMed ID: 8307573; 23. Hansen, L. L.; Brown, G. K.; Kirby, D. M.; Dahl, H.-H. M. Characterization of the mutations in three patients with pyruvate dehydrogenase E1-alpha deficiency. J. Inherit. Metab. Dis. 14: 140–151, 1991. PubMed ID: 1909401; 24. Harris, E. E.; Hey, J. X chromosome evidence for ancient human histories. Proc. Nat. Acad. Sci. 96: 3320–3324, 1999. PubMed ID: 10077682; 25. Ho, L.; Wexler, I. D.; Liu, T.-C.; Thekkumkara, T. J.; Patel, M. S. Characterization of cDNAs encoding human pyruvate dehydrogenase alpha subunit. Proc. Nat. Acad. Sci. 86: 5330–5334, 1989. PubMed ID: 2748588; 26. Huq, A. H. M. M.; Ito, M.; Naito, E.; Saijo, T.; Takeda, E.; Kuroda, Y. Demonstration of an unstable variant of pyruvate dehydrogenase protein (E1) in cultured fibroblasts from a patient with congenital lactic acidemia. Pediat. Res. 30: 11–14, 1991. PubMed ID: 1909778; 27. Ito, M.; Huq, A. H. M. M.; Naito, E.; Saijo, T.; Takeda, E.; Kuroda, Y. Mutation of E1-alpha gene in a female patient with pyruvate dehydrogenase deficiency due to rapid degradation of E1 protein. J. Inherit. Metab. Dis. 15: 848–856, 1992. PubMed ID: 1338114; 28. Kerr, D. S.; Berry, S. A.; Lusk, M. M.; Ho, L.; Patel, M. S. A deficiency of both subunits of pyruvate dehydrogenase which is not expressed in fibroblasts. Pediat. Res. 24: 95–100, 1988. PubMed ID: 3137520; 29. Lissens, W.; De Meirleir, L.; Seneca, S.; Benelli, C.; Marsac, C.; Poll-The, B. T.; Briones, P.; Ruitenbeek, W.; van Diggelen, O.; Chaigne, D.; Ramaekers, V.; Liebaers, I.:Mutation analysis of the pyruvate dehydrogenase E(1)a gene in eight patients with a pyruvate dehydrogenase complex deficiency. Hum. Mutat. 7: 46–51, 1996. PubMed ID: 8664900; 30. Lissens, W.; De Meirleir, L.; Seneca, S.; Liebaers, I.; Brown, G. K.; Brown, R. M.; Ito, M.; Naito, E.; Kuroda, Y.; Kerr, D. S.; Wexler, I. D.; Patel, M. S.; Robinson, B. H.; Seyda, A. Mutations in the X-linked pyruvate dehydrogenase (E1) alpha subunit gene (PDHA1) in patients with a pyruvate dehydrogenase complex deficiency. Hum. Mutat. 15: 209–219, 2000. PubMed ID: 10679936; 31. Lissens, W.; Vreken, P.; Barth, P. G.; Wijburg, F. A.; Ruitenbeek, W.; Wanders, R. J. A.; Seneca, S.; Liebaers, I.; De Meirleir, L. Cerebral palsy and pyruvate dehydrogenase deficiency: identification of two new mutations in the E1-alpha gene. Europ. J. Pediat. 158: 853–857, 1999. PubMed ID: 10486093; 32. Livingstone, I. R.; Gardner-Medwin, D.; Pennington, R. J. T. Familial intermittent ataxia with possible X-linked recessive inheritance: two patients with abnormal pyruvate metabolism and a response to acetazolamide. J. Neurol. Sci. 64: 89–97, 1984. PubMed ID: 6539810; 33. Matthews, P. M.; Brown, R. M.; Otero, L.; Marchington, D.; Leonard, J. V.; Brown, G. K. Neurodevelopmental abnormalities and lactic acidosis in a girl with a 20-bp deletion in the X-linked pyruvate dehydrogenase E1-alpha subunit gene. Neurology 43: 2025–2030, 1993. PubMed ID: 7692352; 34. Matthews, P. M.; Brown, R. M.; Otero, L. J.; Marchington, D. R.; LeGris, M.; Howes, R.; Meadows, L. S.; Shevell, M.; Scriver, C. R.; Brown, G. K. Pyruvate dehydrogenase deficiency: clinical presentation and molecular genetic characterization of five new patients. Brain 117: 435–443, 1994. PubMed ID: 8032855; 35. Matthews, P. M.; Marchington, D. R.; Squier, M.; Land, J.; Brown, R. M.; Brown, G. K. Molecular genetic characterization of an X-linked form of Leigh's syndrome. Ann. Neurol. 33: 652–655, 1993. PubMed ID: 8498846; 36. Olson, S.; Song, B. J.; Huh, T.-L.; Chi, Y.-T.; Veech, R. L.; McBride, O. W. Three genes for enzymes of the pyruvate dehydrogenase complex map to human chromosomes 3, 7, and X. Am. J. Hum. Genet. 46: 340–349, 1990. PubMed ID: 1967901; 37. Otero, L. J.; Brown, G. K.; Silver, K.; Arnold, D. L.; Matthews, P. M. Association of cerebral dysgenesis and lactic acidemia with X-linked PDH E1-alpha subunit mutations in females. Pediat. Neurol. 13: 327–332, 1995.; 38. Otero, L. J.; Brown, R. M.; Brown, G. K. Arginine 302 mutations in the pyruvate dehydrogenase E1-alpha subunit gene: identification of further patients and in vitro demonstration of pathogenicity. Hum. Mutat. 12: 114–121, 1998. PubMed ID: 9671272; 39. Patel, M. S.; Harris, R. A. Mammalian alpha-keto acid dehydrogenase complexes: gene regulation and genetic defects. FASEB J. 9: 1164–1172, 1995. PubMed ID: 7672509; 40. Robinson, B. H.; MacMillan, H.; Petrova-Benedict, R.; Sherwood, W. G. Variable clinical presentation in patients with defective E1 component of pyruvate dehydrogenase complex. J. Pediat. 111: 525–533,1987. PubMed ID: 3116190; 41. Seyda, A.; McEachem, G.; Haas, R.; Robinson, B. H. Sequential deletion of C-terminal amino acids of the E1-alpha component of the pyruvate dehydrogenase (PDH) complex leads to reduced steady-state levels of functional E1-alpha-2-beta-2 tetramers: implications for patients with PDH deficiency. Hum. Molec. Genet. 9: 1041–1048, 2000. PubMed ID: 10767328; 42. Shevell, M. I.; Matthews, P. M.; Scriver, C. R.; Brown, R. M.; Otero, L. J.; Legris, M.; Brown, G. K.; Arnold, D. L. Cerebral dysgenesis and lactic acidemia: an MR1/MRS phenotype associated with pyruvate dehydrogenase deficiency. Pediat. Neuro. 11: 224–229, 1994.; 43. Szabo, P.; Rex Sheu, K.-F.; Robinson, R. M.; Grzeschik, K.-H.; Blass, J. P. The gene for the alpha polypeptide of pyruvate dehydrogenase is X-linked in humans. Am. J. Hum. Genet. 46: 874–878, 1990. PubMed ID: 2339687; 44. Takakubo, F.; Cartwright, P.; Hoogenraad, N.; Thorbum, D. R.; Collins, F.; Lithgow, T.; Dahl, H.-H. M. An amino acid substitution in the pyruvate dehydrogenase E1-alpha gene, affecting mitochondrial import of the precursor protein. Am. J. Hum. Genet. 57: 772–780, 1995. PubMed ID: 7573035; 45. Takakubo, F.; Thorburn, D. R.; Dahl, H.-H. M. A four-nucleotide insertion hotspot in the X chromosome located pyruvate dehydrogenase E1-alpha gene (PDHA1). Hum. Molec. Genet. 2: 473–474, 1993. PubMed ID: 8504309; 46. Wexler, I. D.; Hemalatha, S. G.; Liu, T.-C.; Berry, S. A.; Kerr, D. S.; Patel, M. S. A mutation in the E1-alpha subunit of pyruvate dehydrogenase associated with variable expression of pyruvate dehydrogenase complex deficiency. Pediat. Res. 32: 169–174, 1992. PubMed ID: 1508605.

Enzyme proteins, particularly members of the pyruvate dehydrogenase enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the pyruvate dehydrogenase enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the pyruvate dehydrogenase enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain.

DESCRIPTION OF THE FIGURE SHEETS

FIG. 1 provides the nucleotide sequence of a cDNA molecule that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 22 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the pyruvate dehydrogenase enzyme subfamily. Utilizing these sequences, additional genomic sequences were assembled and transcript and/or cDNA sequences were isolated and characterized. Based on this analysis, the present invention provides amino acid sequences of human enzyme peptides and proteins that are related to the pyruvate dehydrogenase enzyme subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the pyruvate dehydrogenase enzyme subfamily and the expression pattern observed. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known pyruvate dehydrogenase family or subfamily of enzyme proteins.

Specific Embodiments

Peptide Molecules

The present invention provides nucleic acid sequences that encode protein molecules that have been identified as being members of the enzyme family of proteins and are related to the pyruvate dehydrogenase enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can he accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Human Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunech (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWS gapdna CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome X (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome X (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme protein of the present invention. SNPs were identified at 22 different nucleotide positions, including non-synonymous coding SNPs at 18 nucleotide positions. Changes in the amino acid sequence caused by these SNPs is indicated in FIG. 3 and can readily be determined using the universal genetic code and the protein sequence provided in FIG. 2 as a reference. The SNPs located 5' of the ORF and in introns may affect control/regulatory elements.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention. A large percentage of pharmaceutical agents are being developed that modulate the activity of enzyme proteins, particularly members of the pyruvate dehydrogenase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the pyruvate dehydrogenase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype.

The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes 1 mmol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), para-logs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome X (as indicated in FIG. 3), which is supported by multiple lines of evidence, such as STS and BAC map data.

FIG. 3 provides information on SNPs that have been found in the gene encoding the enzyme protein of the present invention. SNPs were identified at 22 different nucleotide positions, including non-synonymous coding SNPs at 18 nucleotide positions. Changes in the amino acid sequence caused by these SNPs is indicated in FIG. 3 and can readily be determined using the universal genetic code and the protein sequence provided in FIG. 2 as a reference. The SNPs located 5' of the ORF and in introns may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2× SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 22 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome X (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, colon adenocarcinoma, and fetal brain.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme protein of the present invention. SNPs were identified at 22 different nucleotide positions, including non-synonymous coding SNPs at 18 nucleotide positions. Changes in the amino acid sequence caused by these SNPs is indicated in FIG. 3 and can readily be determined using the universal genetic code and the protein sequence provided in FIG. 2 as a reference. The SNPs located 5' of the ORF and in introns may affect control/regulatory elements. The gene encoding the novel enzyme of the present invention is located on a genome component that has been mapped to human chromosome X (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al, *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme protein of the present invention. SNPs were identified at 22 different nucleotide positions, including non-synonymous coding SNPs at 18 nucleotide positions. Changes in the amino acid sequence caused by these SNPs is indicated in FIG. 3 and can readily be determined using the universal genetic code and the protein sequence provided in FIG. 2 as a reference. The SNPs located 5' of the ORF and in introns may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzyme proteins of the present invention are expressed in humans in teratocarcinoma of neuronal precursor cells, skin, skin melanotic melanoma, muscle rhabdomyosarcoma, brain neuroblastoma, brain, breast, stomach, pancreas adenocarcinoma, uterus serous papillary carcinoma, brain anaplastic oligodendroglioma, and colon adenocarcinoma, as indicated by virtual northern blot analysis, and in fetal brain, as indicated by the tissue source of the cDNA clone of the present invention. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme protein of the present invention. SNPs were identified at 22 different nucleotide positions, including non-synonymous coding SNPs at 18 nucleotide positions. Changes in the amino acid sequence caused by these SNPs is indicated in FIG. 3 and can readily be determined using the universal genetic code and the protein sequence provided in FIG. 2 as a reference. The SNPs located 5' of the ORF and in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, An Introduction to Radioimmunoassay and Related Techniques, Elsevier Science Publishers, Amsterdam, The Netherlands (1986); Bullock, G. R. et al, *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxyiruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al, *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of S cerevisiae (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. A nucleic acid vector comprising the nucleic acid molecule of claim 1.

3. A host cell containing the vector of claim 2.

4. A process for producing a polypeptide comprising culturing the host cell of claim 3 under conditions sufficient forte production of said polypeptide, and recovering said polypeptide.

5. An isolated polynucleotide consisting of the nucleotide sequence of SEQ ID NO:1.

6. An isolated polynucleotide consisting of the nucleotide sequence of SEQ ID NO:3.

7. The vector of claim 2, wherein said vector is selected from the group consisting of a plasmid, a virus, and a bacteriophage.

8. The vector of claim 2, wherein said isolated nucleic acid molecule is inserted into said vector in proper orientation and correct reading frame such that a polypeptide comprising SEQ ID NO:2 may be expressed by a cell transformed with said vector.

9. The vector of claim 8, wherein said isolated nucleic acid molecule is operatively linked to a promoter sequence.

10. An isolated nucleic acid molecule comprising a nucleotide sequence selected from the group consisting of:
    (a) a cDNA sequence that encodes SEQ ID NO:2;
    (b) SEQ ID NO:1;
    (c) nucleotides 90–1280 of SEQ ID NO:1; and
    (d) a nucleotide sequence that is completely complementary to a nucleotide sequence of (a)–(c).

11. A nucleic acid vector comprising the nucleic acid molecule of claim 10.

12. A host cell containing the vector of claim 11.

13. A process for producing a polypeptide comprising culturing the host cell of claim 12 under conditions sufficient for the production of said polypeptide, and recovering said polypeptide.

14. The vector of claim 11, wherein said vector is selected from the group consisting of a plasmid, a virus, and a bacteriophage.

15. The vector of claim 11, wherein said isolated nucleic acid molecule is inserted into said vector in proper orientation and correct reading frame such that a polypeptide comprising SEQ ID NO:2 may be expressed by a cell transformed with said vector.

16. The vector of claim 15, wherein said isolated nucleic acid molecule is operatively linked to a promoter sequence.

17. An isolated nucleic acid molecule encoding a pyruvate dehydrogenase E1-alpha subunit, wherein the nucleic acid molecule consists of a nucleotide sequence selected from the group consisting of:
    (a) a nucleotide sequence that encodes an amino acid sequence having at least 99% sequence identity to SEQ ID NO:2;
    (b) a nucleotide sequence having at least 99% sequence identity to SEQ ID NO:1; and
    (c) a nucleotide sequence having at least 99% sequence identity to SEQ ID NO:3.

18. A nucleic acid vector comprising the nucleic acid molecule of claim 17.

19. A host cell containing the vector of claim 18.

20. A process for producing a polypeptide comprising culturing the host cell of claim 19 under conditions sufficient for the production of said polypeptide, and recovering said polypeptide.

21. At The vector of claim 18, wherein said vector is selected from the group consisting of a plasmid, a virus, and a bacteriophage.

22. The vector of claim 18, wherein said isolated nucleic acid molecule is inserted into said vector in proper orientation and correct reading frame such that a pyruvate dehydorgenase E1-alpha subunit polypeptide having at least 99% sequence identity to SEQ ID) NO:2 may be expressed by a cell transformed with said vector.

23. The vector of claim 22, wherein said isolated nucleic acid molecule is operatively linked to a promoter sequence.

24. An isolated nucleic acid molecule consisting of a nucleotide sequence that is completely complementary to a nucleotide sequence of claim 17.

* * * * *

SEQUENCE LISTING

<160> NUMBER OF SEQ ID NOS: 6

<210> SEQ ID NO 1
<211> LENGTH: 1546
<212> TYPE: DNA
<213> ORGANISM: Human

<400> SEQUENCE: 1

```
tgctggggca cctgaaggag acttgggggc acccgcgtcg tgcctcctgg gttgtgagga      60
gtcgccgctg ccgccactgc ctgtgcttca tgaggaagat gctcgccgcc gtctcccgcg     120
tgctgtctgg cgcttctcag aagccggcaa gcagagtgct ggtagcatcc cgtaattttg     180
caaatgatgc tacatttgaa attaagaaat gtgaccttca ccggctggaa gaaggccctc     240
ctgtcacaac agtgctcacc agggaggatg ggctcaaata ctacaggatg atgcagactg     300
tacgccgaat ggagttgaaa gcagatcagc tgtataaaca gaaaattatt cgtggtttct     360
gtcacttgtg tgatggtcag tttctccttc ctctaacaca ggaagcttgc tgtgtgggcc     420
tggaggccgg catcaacccc acagaccatc tcatcacagc ctaccgggct cacggctttα     480
ctttcacccg gggcctttcc gtccgagaaa ttctcgcaga gcttacagga cgaaaaggag     540
gttgtgctaa agcgaaagga ggatcgatgc acatgtatgc caagaacttc tacggggca      600
atggcatcgt gggagcgcag gtgccctgg cgctgggat tgctctagcc tgtaagtata      660
atggaaaaga tgaggtctgc ctgactttat atggcgatgt gctgctaac cagggccaga      720
tattcgaagc ttacaacatg gcagctttgt ggaaattacc ttgtattttc atctgtgaga     780
ataatcgcta tggaatggga acgtctgttg agagagcggc agccagcact gattactaca     840
agagaggcga tttcattcct gggctgagag tggatggaat ggatatcctg tgcgtccgag     900
aggcaacaag gtttgctgct gcctattgta gatctgggaa ggggcccatc ctgatggagc     960
tgcagactta ccgttaccac ggacacagta tgagtgaccc tggagtcagt taccgtacac    1020
gagaagaaat tcaggaagta agaagtaaga gtgaccctat tatgcttctc aaggacagga    1080
tggtgaacag caatcttgcc agtgtggaag aactaaagga aattgatgtg aagtgagga     1140
aggagattga ggatgctgcc cagttttgcca cggccgatcc tgagccacct ttggaagagc    1200
tgggctacca catctactcc agcgacccac cttttgaagt tcgtggtgcc aatcagtgga    1260
tcaagtttaa gtcagtcagt taaggggagg agaaggagag gttatacctt caggggggta    1320
ccagacagtg ttctcaactt ggttaaggag gaagaaaacc cagtcaatga aattcaatga    1380
aattcttgga aacttccatt aagtgtgtag attgagcagg tagtaattgc atgcagtttg    1440
tacattagtg cattaaaaga tgaattattg agtgcttaaa aaaaaaaaa aaaaaaaaa      1500
aaaaaaaaa aaaaaaaaa aaaaaaaaa aaaaaaaaa aaaaaa                       1546
```

<210> SEQ ID NO 2
<211> LENGTH: 397
<212> TYPE: PRT
<213> ORGANISM: Human

<400> SEQUENCE: 2

Met Arg Lys Met Leu Ala Ala Val Ser Arg Val Leu Ser Gly Ala Ser
 1               5                  10                  15

Gln Lys Pro Ala Ser Arg Val Val Ala Ser Arg Asn Phe Ala Asn
            20                  25                  30

Asp Ala Thr Phe Glu Ile Lys Lys Cys Asp Leu His Arg Leu Glu Glu

-continued

```
                35                  40                  45
Gly Pro Val Thr Thr Val Leu Thr Arg Glu Asp Gly Leu Lys Tyr
 50                  55                  60
Tyr Arg Met Met Gln Thr Val Arg Arg Met Glu Leu Lys Ala Asp Gln
 65                  70                  75                  80
Leu Tyr Lys Gln Lys Ile Ile Arg Gly Phe Cys His Leu Cys Asp Gly
                 85                  90                  95
Gln Phe Leu Leu Pro Leu Thr Gln Glu Ala Cys Val Gly Leu Glu
                100                 105                 110
Ala Gly Ile Asn Pro Thr Asp His Leu Ile Thr Ala Tyr Arg Ala His
                115                 120                 125
Gly Phe Thr Phe Thr Arg Gly Leu Ser Val Arg Glu Ile Leu Ala Glu
                130                 135                 140
Leu Thr Gly Arg Lys Gly Gly Cys Ala Lys Ala Lys Gly Gly Ser Met
145                 150                 155                 160
His Met Tyr Ala Lys Asn Phe Tyr Gly Gly Asn Gly Ile Val Gly Ala
                165                 170                 175
Gln Val Pro Leu Gly Ala Gly Ile Ala Leu Ala Cys Lys Tyr Asn Gly
                180                 185                 190
Lys Asp Glu Val Cys Leu Thr Leu Tyr Gly Asp Gly Ala Ala Asn Gln
                195                 200                 205
Gly Gln Ile Phe Glu Ala Tyr Asn Met Ala Ala Leu Trp Lys Leu Pro
                210                 215                 220
Cys Ile Phe Ile Cys Glu Asn Asn Arg Tyr Gly Met Gly Thr Ser Val
225                 230                 235                 240
Glu Arg Ala Ala Ala Ser Thr Asp Tyr Tyr Lys Arg Gly Asp Phe Ile
                245                 250                 255
Pro Gly Leu Arg Val Asp Gly Met Asp Ile Leu Cys Val Arg Glu Ala
                260                 265                 270
Thr Arg Phe Ala Ala Ala Tyr Cys Arg Ser Gly Lys Gly Pro Ile Leu
                275                 280                 285
Met Glu Leu Gln Thr Tyr Arg Tyr His Gly His Ser Met Ser Asp Pro
                290                 295                 300
Gly Val Ser Tyr Arg Thr Arg Glu Glu Ile Gln Glu Val Arg Ser Lys
305                 310                 315                 320
Ser Asp Pro Ile Met Leu Leu Lys Asp Arg Met Val Asn Ser Asn Leu
                325                 330                 335
Ala Ser Val Glu Glu Leu Lys Glu Ile Asp Val Glu Val Arg Lys Glu
                340                 345                 350
Ile Glu Asp Ala Ala Gln Phe Ala Thr Ala Asp Pro Glu Pro Pro Leu
                355                 360                 365
Glu Glu Leu Gly Tyr His Ile Tyr Ser Ser Asp Pro Pro Phe Glu Val
                370                 375                 380
Arg Gly Ala Asn Gln Trp Ile Lys Phe Lys Ser Val Ser
385                 390                 395

<210> SEQ ID NO 3
<211> LENGTH: 18400
<212> TYPE: DNA
<213> ORGANISM: Human
<220> FEATURE:
<221> NAME/KEY: misc_feature
<222> LOCATION: (1)...(18400)
<223> OTHER INFORMATION: n = A,T,C or G

<400> SEQUENCE: 3
```

-continued

```
agttgttcct tctaacccat tgatttgttc aatcatgtat ttaagtagga cctatatttt      60
acttgttcct tgctatatct tcagtgtgta gtacagtgtc tgacacaaaa tcggtgctca     120
ataataggtg ttggatgaat gagcaaatga atgaatgaat tcatattcat atggcctaca     180
gagttcccgt acatgcacaa ccaatatcac caccccgtgg agatgactcc caaattaata     240
tttttagcaa atgttccaga cttacaactc caacttcccg ggggacatct tcagatagct     300
gtgccactgc caccaccagg tcaacatgtc ccaaaccatt cagaccagct ttttctcctg     360
agctggacat ctggcctcca accttttcat tctcttttac ctttcatatt ctatcagcag     420
cagcagctgc tgaaatcata ccatgcaagt ttctcacgtc catctctgcc ttttaatggc     480
gccctctcac tcctttaaga agttttcttc cactgcaaca cgatctctca gtccagagtc     540
tggcccagtg cccaaattat ttctctagct atgctgagag ctggtcatgc tttgaacttc     600
tgctttgaat actttcagtg acactgggag agaattatct cattggacca ttgtcattgt     660
tagaaaattc attgttatgc tgaaatgaaa tgatttttatt cacacacaca cacacacaca     720
cacaaaatag ctcttcctcc tggaacatga ctggcctgaa aatgtgtgaa gacatatcca     780
atcctctctg gttttactgt tcatccaatt ttctgttctc ctcctggcag gaggattata     840
tttcaccttg tggaactcag acatggtcgg gtaactagct ctggtccgtg aaaattgaga     900
ggaagtgaca tgtgtcactt ctgggcagaa gctttgagag ccggtttaaa tgatcccttt     960
tctcttcatc catgagacaa gctaagttcc agagagaggg tgccacgctg tgagggacct    1020
gtgttacgag tacgatggct cgcgtcactt caaattcttg aaatcactga aatttggagg    1080
tcagttgtta catcataacc cagccaattc tagttagcct gttttcttcc taacttcttt    1140
aatcgttctt cataagtcac aatcgcagcc cctcaccgtt ctgaccactg tccctggat    1200 tccactcagt ttactcatta tccccttaa aatgtggagc ccaaatctga acccggaacc    1260
ccaggtgcaa tcccactagg acacaacaca atgggttcct gagccctttg atcctctgaa    1320 tagagccct tgttgctttg gtgttttgtc tctgtgtgtg cttttatcat cggctgagcc    1380
acgctgttaa ctcgcagtga gcctgtgaac caataactag agaaaaaaga tttttcccat    1440
tgtcctctcg acatatattg ggaaacaaat tttttgatcc gcgttcaagt agacagggca    1500
gaactgtcca actgctacgt gatctttaa agacaaagtt agtggcagac catttacaga    1560
aaccagatgt tctgtctttt ggctctgagc atgctgctaa tcttcatcat ctagtgtact    1620
gaacgagatg tactgaacga gggctgcaga gctgcagcac cggcaggagt aggcgctcgg    1680
taggacgggg cctgcacaac ctccccggta gtcagcagag cggaatctag gaaggctcct    1740
ttcccgcggc gccctggagg cggggcccc accttcccac gcaggcgcta tcaagccccg    1800
cctcctcacc cgcccgcggc gtggcgtcgg aaagagccct cagcccctcc ctctctggcg    1860
ctgataccca atgggcagcc tcaggccttt agcgggggcg gggcacccc tggacgccgt    1920 tctggttggc ccgcggcccg gcgcagcgca tgacgttatt acgactctgt cacgccgcgg    1980
tgcgactgag gcgtggcgtc tgctgggca cctgaaggag acttggggc acccgcgtcg    2040 tgcctcctgg gttgtgagga gtcgccgctg ccgccactgc ctgtgcttca tgaggaagat    2100
gctcgccgcc gtcccgcgcg tgctgtctgg cgcttctcag aagccggtga gacctcccgg    2160
gcgggccggg atggggcgcg agtggggctg aggcggggcc ggagggcagg gcgggccagg    2220
ccgggccacc cagagcgggg tggaaggcgc caggggagcc gggagccctt tacttcgcct    2280 ccgcgcccctg cattccgttc ctggcctcgg gagaagcggc acggaccggg atcacgccaa    2340
```

-continued

```
ggtccgtgtg aacttccccc ttctcgacac ccacctcccg cccccgggcc cagctgtgcg    2400
ccaggcgaag tcggtgtgct caagaggtgc ctgttgggtt acaggacacg gaaagggtgg    2460
cctcggcctc cttcgagtct ccaattgacc ccactcattt cggatcttct aacttaattt    2520 ctccttgaccg agaggctttg taatagcgta gaatctggag acagggtggc ttcgttcaaa    2580
cagcaccctc accattgact agccctgtga ccttgagcaa gttttttaaac gtcccgggga    2640 cccggtttcc taaaatgttt gctcgaagtg gagttaatct ctaaatggag ataagagtta    2700
tctctgaaat gttatcggtt attaaaatgt tatcagttaa ctctaaaatg gagataataa    2760
gagtccccac ctcttggggt tgtcttgagg attcaacgag tgacacgtgt ggaaacgatt    2820
ccaaatagca cctggcacat aatcgataac atgtgtgttg aatagtgtta tttattgagt    2880
ctccagttcg gtatacattt cttgaacacc tgtgctcagt tctgaggcgg gttcacagaa    2940
ggtcagcctc ttcagaaaca aacttcctcc tcttccctct ccctcaacat ctgagctttt    3000
cttggcagtg agttcaggag cgccgaagca gaactcagag gacgctgccc tcccctcccc    3060
ttacctacac attcttaggg tacaagtagc taaagcaaag agcaacgatg cttgaggggt    3120 gggggggtaga gtttagcact atttcatggc ctcagcattt agaggtgcct aacacctgag    3180
ctagcattct gaccccccta ggcacagtga ggtcgtgtta attggtgtaa ctgcaggcct    3240
cgggattctg gtatttcccc caggacttga taccgctcta cttagtacag gcaagagatt    3300
gtcaaaaggt aaagaggtat gcccctctag gaatcctgtt gcctaaaata atgacaaaac    3360
tgccgggtgc ggtgctcagg cctgtaatcc cagcattttg ggaggctgag gcaggtggat    3420
cacctgaagg tcagaagttc gagatcagcc tggccaacat ggtgaaaccc cgtctctact    3480
aaaaatacaa aattagccgg tcgtggtggc gggctcctgt aatcccagct actcgggagg    3540
ctgaggcggg agaatagcct gaacccggga gcggagtttg cagtgagcgg agatcgtgcc    3600
attgcactac ggcctgggcg acaagaagca agaactccgt atttttaaaaa aaaaaaaaaa    3660 aaaaaaaaaa aaaagcgttc cctttaggga tatctgtggg tagagggctg taccggtagt    3720
tacgggctca gaaacatcct tcctttaggc acctgatgta ggttttcttc ttcttctgca    3780
agtcaggttc attgtttcct gtatcagttt gcagggtccc ccccccccg ccaccttaca    3840 gtaggaagaa aattgagttc cagatatgaa gtcacctttg aaagtgccca ggtatctttc    3900
cacttggtgg tgtaaactct tcagataatt agaagttttc tgtgtcactc aacttgtcat    3960
ggactaattt aggaaacatt cctgaagctt ttaaggatag aactaaaagt ttcactttta    4020 ttttttttaaa gggtggaata ataaactaac gtgttgactc tttgtatttt gtaattcttc    4080
atacttatgg atgtcttttt acttaactat aagtaacaaa atagatcaac gttttagttt    4140
ttttatatta tacatgtaaa aagacatttt gcatataagc ctttcacaaa aatcttgaca    4200
gtaaacaata agcagtggct cacccaaatt aggcagactt actgcactag actcctacca    4260
tctgtgtgat actccatgaa gggagggaga aggggaggga gaagggtagg cagctggtct    4320
gatggctgtg acacaagata atcccccttaa cctcccaaga cgctgtgtgt tttttccttt    4380
tttattctcc ctggtttact ttcgttttgt ttgagacagg gtctctgtgt cacccaggct    4440
ggagtgcagt agcaggacag ctcactgcag ccttagcctg ctgggctcaa gcgatcctcc    4500
tgccttagcc tcctgagtag ctgggaacac aggcatgtgc caccaccaca cccagccaat    4560
taaaaaaatt ttttttttac tagagacatg gtccttgctac gttgcccagt ctggtctcca    4620
tctccaggct caagcagtcc tcccacctcg gcctcccaaa gtgctgggat tactctcact    4680
ctcttaaaac caggcaggta gggagattta tctcaggctt aaagattgcc attgtctcat    4740
```

```
caaagagtgt tggtgtgaa actttgaaat gaatatcaag attgtgtttt tattttgaa    4800
taaggtttat agttttcata gttcttattt catggaagaa gattgaatgc atttaaaatg    4860
ttattttatt gtttgcattt ctgtatggct ccttttgtga gatctttact agcaatgttt    4920
tggctttata agtggtaggt aagagtttta atttacactg ttagaatctg gaatttttga    4980
aacgttttc ctctttcaca tgaatggttc ctatgtattt aggaagttaa agttttactt    5040
tttttttaatt aatttttttt tttaggctgg aatgcagtgg cacagtcata gctcactgta    5100
gcctcaggtg tgtgccacca tacctgacta atttttttaat atttattttt gtagagatga    5160
gagtctcatg ttgcccaggc tggctttgaa ctcctggctt caagtggtcc tcccaccctg    5220
gcctcccaaa gtgctgggga ttataggtgt gagccatcat gcccggccta gttttttattt    5280
tttaaaattt gagtgggttg ttcgtggtct ctgtcagaga ggaatcccat ttaacagaga    5340
atcttttttat ggctctccag agaaaatgaa tggtaaactt atcttttcaa caagctctca    5400
ctcagaaatg atacacacac acttctgata ggacttttag cttctttaac tttgttcctt    5460
tcactcatat cagtggttct tatttttgag atacacagta atgaagccat gggagaaagt    5520
atctaagtag ctttctggca gtcctaatct ttgcaggcgc aagattacag gcgcatgcca    5580
cagcactggg ccccttcttg ctctttattg tatagcatta tcctgcctca ttgtttcaac    5640
tctaggattg agaaagaagt tacctttttct ctgttactgt cgcctggctg gtttggactc    5700
ctgccttcca aaaactgcag tttctgtagt tgtatttgga aatttattc acaatacaat    5760
aaatttctgg ccccacaaaa tatttattaa ctgccaagaa taacacatct gtttgattgc    5820
taaatataac cattgatttg ctgtttcacc ttctctcagc tttacttctt cccaaattcc    5880
taaatttcct tcacttttc tgagatacat tagtggactg tctctgcctg taagttaact    5940
gaaacactga ttcctagtat ttcagttgtt ttcctccagc actgtcattg tctgtgtttg    6000
ttggctttgt ccaataatgg tctattgagg ggtgaagata tacgtaatta gctttctgcc    6060
tattggcttg tacactccag ggtatacttg gcagatcagt cttaactctt ctcaccaaga    6120
tcagtccagt gctggattag gtaaggtatg aacacatcag atgtgctttt tatggagaaa    6180
tcatgttggt ttacacgtca gtgtgtgaga atgtggcaga agggagctaa aatagtatga    6240
taatactact ggataaattt tgtggtctaa cctaaacctt agccattaca tagaatactt    6300
ttgctgtgag caggtttgct cagttgtaaa actggaaagg aatcatttct cacccccgc    6360
ctccaagctt tttacctcca aacagtgaca gccacccaaa catcaagaga acagtgtttc    6420
agagaacatt tctactgggg cttcaggagg agcctgtcca agatttaggc tgttcaaatt    6480
ataaattata aaacagctgg ctcaagccca ttgtgtttaa gtcagagagt gctaagtatc    6540
ttttctttg tcttgtctcc ctaaagtatt tatctcatac ttcaatcaat ttaaaatatt    6600
ttttcttaca gatccaattt gatagaagag tcaagtttgc ctagagtgga gattaaatca    6660
tagttttatt tgaagtataa ttttggcttg ctcaaaatga acagtatctg gttatgacta    6720
agaatggcat gaaaaggcca gacgcagtgg ctcatgcctg caatcccagt actttgggag    6780
gccaaggcag gtggatcacc tgaggtcagg agttggagac cagcctggcc aacatggtga    6840
aaccccatct ctactaaaaa tataaaaatt agccgggccg tggtggtggg cacctgtaat    6900
cccagctact cgggagactg agacaggaga atcacttga acccgggaag cggaggttgc    6960
agtgagccga atcgcacca ctgcactcca gcctgggtga taaaagcaaa actccgtctc    7020
aaaacaaaca aacaaaagaa tggcataaac agacacagct cacagatgat ctagtctctt    7080
```

```
tagccactaa tttcattata ttctcactat aatttctttg aaaacaaagg atgggtttgt   7140 ttttttgcccc tctttgcgct gcttgccttc agatgcggga taatcctgtt tcattggcca  7200
aagcatggat tcattttgga ggccaaggaa gatgcaaaca cagtgcacag ggtggaagag   7260
aagcctatga atatgttggg gcttattaaa tttccataac ttcattctga taactgatta   7320
ttatactttc caaaatagct gacaattaaa aagtactgat ttgtttgtat atttttgtct   7380
tttaaggcaa gcagagtgct ggtagcatcc cgtaattttg caaatgatgc tacatttgaa   7440
attaaggtaa gagtgtttta ctttgttaat aatttttca caggtacact ctgatataca    7500
gttttacctt tagaatagaa catcttgatg ttcatgatta gtcatcattt tcttctaaat   7560
gtccaggatc agaagttcag agaagcttat tcaaaagttt ggaatgtaat tcagtgaaat   7620
atttgaataa gaagagtctt agttgtttct ttgaaggttc tttcaaccta taactcagtt   7680
ggcttctagg ggctttcagt gaaaatcatc ttagaaagat ttccttcccc caagccccat   7740
ctcattgcac agtgaggttt atggatttaa ggaacagagg cgatatgaag cattactgat   7800
gtgctccttt gcagtttttc aagttcaata ttatttgcaa tggagttaga tcttagagtg   7860
gtcaacagtg tttgcaatgt agtatgtgga ggataataac taccttattc catttcagaa   7920
atgtgacctt caccggctgg aagaaggccc tcctgtcaca acagtgctca ccagggagga   7980
tgggctcaaa tactacagga tgatgcagac tgtacgccga atggagttga aagcagatca   8040
gctgtataaa cagaaaatta ttcgtggttt ctgtcacttg tgtgatggtc aggtgagtgg   8100
taggtttgtg gtggaactgt gttatttagg tactgaagta tggcttgtac ttattgggct   8160
ttaccctgcc atatgtatca gaagagtttg aggctggtaa tgtaattttc ttttattat   8220 tattttttt gagacagtct ctctctgtcg cccaggttag agtacagtgg tgatcttggc   8280
tcactgcagc ctctggttag agtacagtgt gatcttggct cactgcagcc tctgtccact   8340
gggctcaagc aatcctccca cctcagcctc ccgagtatgt gggaccacag gtgcacacca   8400
acacacccag ctaattttg tattttttgg agatacgggg tttcactatg ttgcccaggc    8460
tagtctcaaa cttctgggct caagtggtcc gcccaccttg gcctcccaag gtgctaggat   8520
tacaggcgtg agccactgtg cctggctgaa gccagtattt tagaattaaa aagtagaatg   8580
ccaaaacctg ctatgaagct taggctaaag aattcattca cacataacat tgccagtttt   8640
ctgtacctgt tcttagagtt ttactatttt aaaactttct ggcactatga tcgcctgtac   8700
tgtatataat ttggagagaa aggattagtt tgttttttgt tttgtgggct taggtcaagg   8760
gttagagtca aataccctaca agggccagcc aggtagaata aatgagtgaa gaaggctagg   8820
tatacaaaac agaaaatggt gacagggact catgctgaac tggcaccagc atgccctacc   8880
cagaggaatg ccatgacttg gttccagcca gttggtgcca tgtggaaatc agggtaatg    8940 tttcctgttt tccatgtcta agagaaggcg gaagtctgga ttttcatgtg aaattcccag   9000
tgttttaatg ttgacatctg atgtaggctt ttattttagg tcatcataca ggagaaagga   9060
aggaagtggc acatgtgtgg gttgccagtt tattgcttct ggtttgggcc ttccactctg   9120 tatttgggg gaaaatagct actttctctg gttattaatg acagggtcta ctagcccaca   9180
tatttcactg tggtctagga aacgttttta tttagaaaca tgtatcatat tgcctcatag   9240
tttctccttc ctctaacaca ggaagcttgc tgtgtgggcc tggaggccgg catcaacccc   9300
acagaccatc tcatcacagc ctaccgggct cacggcttta ctttcacccg ggccttttcc   9360
gtccgagaaa ttctcgcaga gcttacaggt ttgctgttga tttacagaaa ggggaaatga   9420
gtggattaag ttttttaaata tctgtgcatt aagatgctat tatgagttaa tatttgttaa   9480
```

```
aaattttaag ttttctttttt taaccctctc tcctttggtg ctctggtact tctgttgtgc   9540
tcttgagtta actgaccatt tgtgaagttc tctggcccct caggtaaaag tttaaaacag   9600
gttggtgcta taaaatcaca gtaggtttgg ttatcattca agcatgccag aagaagtcta   9660
gcagtcatag aaagtaagtt cggttgaagc actccatggt atgcaatgta aattctagaa   9720
atcttcttaa tattcccctt ttctttgtcc cccgtgacta tttgtttgtt ttggtggttt   9780
tttttttttt tttttttga gactgtgtct cactccgttg tccaggtggt gtgcagtggt   9840
gtgatcaggg ctcactgcaa cctccacctc ccgggttcaa gtgattctca tgcctccacc   9900
tcctgagtag ctgggactac aggcatgcac caccacacct ggctaatttt tgtattttta   9960
gtagagatgg ggtttcaaca tgttggccag gctggtctcc aactcctgac ctcaggtgat  10020
ccacctgcct tggcctccca agtgtgctg gggttacagg cgtgagccac cgcacctggc  10080
ctgttttgtt tttttgagac agagtctcgc tttgttgccc aggctggagt gcagtggcct  10140
gcctcagcct cccaaaatgc taggattaca ggcgtgagcc actgtgcccg tcctcctcc   10200 tcctcctttt tttttttttt ttttgagaca gagtttcact ctttcaccca ggctggagtg  10260
gctggagtga agtggtatga ttttggctca ctgcagcctc cgcccccgg gttcaagcaa   10320 ttctcctgcc tcagcctcct gagtagctag gattataggt gcccaaccac cacacctggc  10380
taatttctgt attttttagta gagaccaggt ttcaccatgt tggccaggct ggtcttgaac  10440
tcttgacctc aggtgatcca ccctcttcgg cctcccaaaa tgttaggatt acaggcgtga  10500
gccgccgtgc ccggccctcc ttgactcttg aactatggtt gtccctctat atatccaggg  10560
gattggttct aggaccctcg agtatacaaa atcctcaaa tactcaagtc ccaaagtcag    10620
ccttccatat cttcgggttt gcatcctgag aatattctat tttcaataca tgtgtggctg  10680
aaaaaaaatc tgtgtataag tgtacctgtg cagttcaaac cctgttcaag gattgaatat  10740
atttagtgta ctagtatagg agaggtccta agatgtttgt aactggccag aaaacccaga  10800
aaagtccagg gtatcatctg gatggaacat ctgaaggaaa ctaagtgact agagagtagg  10860
aaaagctgga aaggttgaag cacatggaac tagtgaaagg acaaggagaa acatgtgttt  10920
gcctggaggg acaggtactt agacgactga actggcctct gtgttctaat ggttgagcct  10980
cagagtacat atttggggtg cggtttggtt tgctttgtag agttggtttg ttctgcacat  11040
gtgtatgttc tgccatttcc aggacgaaaa ggaggttgtg ctaaagggaa aggaggatcg  11100
atgcacatgt atgccaagaa cttctacggg ggcaatggca tcgtgggagc gcaggtagtc  11160
aaggacgagg attgtgtgct gctttagatt tggccctgga ctttgtcttg aaaaaccttt  11220
cacagcccca gacaactttt cctgaagcta gtacagccat gtgctgcaca gtgacgcttt  11280
ggtcaatgtc gcatatatga tgttggaccc ataagattat aatggagctg aaaaattcct  11340
gtcgcctagt gatgttgtag tggcacaaca cattacccttt tctacgttta ggtacacaaa  11400
tattttgcct acaggattca gtagagtcac atgctgtgca gggttgtagc ctaggagcag  11460
taggctctac tatacagcct aggtgtgcag tgggctgtac catctaggtt cgtgcattac  11520
agtatggtgt tcacatgaca aaatcgccta gtgatgcaat tctgagaata tatccctgtt  11580
gttaagtgac gcgtgactat tttggggggct tggtttgctt ttaaagacct agtgcttcat  11640
atcctaccgt ttgagagatg agtagatttg gatggtgatt tataatgttt ccttttaggt  11700
gtctgctgtt ttataagtaa gcaggaacct ctagcagtgg agccatacct tccccttcct  11760
atttatattt cagtacatta attgctttat cttgtcaact tcatttggg gtccttgttc   11820
```

-continued

```
tcatcagtta gtgaatgatg aagaattaac agcacaaaat tatatccgga ctgtttcttt      11880
tcctttctaa tatattaaga ttctattatg tgttgttttt ttttaaacct aggttttatt      11940
tttccttttg aaatggagtc ttgctcagcc gcccaggctg gagcagtggt gtaatctcag      12000
ctcactgcaa cctccacccc cgggttcaag caattctcct gcctcagcct cccgagtagc      12060
tgggaatata gttacgtgcc accatgccca accattttt gtattttag tagagacggg       12120 gtttcaccat cttgtccagg atggtctcga tctgtggacc tcgtgatctg cccaaagtgc      12180
tgggattaca ggcgtgagcc accacgcccg gccaggtttt attttttaac tcttgaatgc      12240
agaaatgtta gtgcttactg gttaaaatag aacatagtat ttatatatta ctttagtgct      12300
ttattgaaaa tatcggaggt gggataaaca gagagatagg gttggaagga gagtttgtag      12360
cagcagtgta atttctgtgt cagattctgg ccaggagtga aaatgcaggg cattaattag      12420
tatctcccct catggatttc tgtggttcct ttctcggttg tccttaatgt taggtgcccc      12480
tgggcgctgg gattgctcta gcctgtaagt ataatggaaa agatgaggtc tgcctgactt      12540
tatatggcga tggtgctgct aaccaggtaa ttatgtctct taacttccca aaaacagtct      12600
tattttcaaa gtctttaata tttacagttg aatttctaaa gaagtagcat attgcttatt      12660
aggtgaaata gcaagtccta tggctagctc aaatttggtt gacttatggc cagattagag      12720
attgacctct tagcgttgtt tcacaagaga cttacggggg cacattcctg tgaaggagct      12780
cacctttgct ctacatcagt gcttggcaaa ggccctgtgg taaaggacct ccccacaacc      12840
tattgcaaaa caatacagac ccattctctt ggatgtccgg gctggcagtg tcaaattcgg      12900
ataatagcgt ctgagtccta actcagtttc tatgcttctc ttgttaccga gtaatcccca      12960
gtctgtggcc agcactctgt gaagcccgt tctagaggct gattcttagg tgctggttca      13020
ctctggctat ccagtgggcc tgatagattt catattgatc ttttttccag tgtgttcctt      13080
actgctagca tggccccaaa gaaacaagta gtagttggtt tgtcaccttc cttagttgca      13140
agagtatgat gcctgctact tctcctccac cacccacccc gctttccctc accacccaaa      13200
gctcggtttt agaagaggag gctttctgtg ctttatgaaa gctttctgtg ccaggcagag      13260
cagcagctgt tagagatgat gaagcctgga gaaagaagcc aaatgaaacc ccttttcgta      13320
actacttcca gggccagata ttcgaagctt acaacatggc agctttgtgg aaattacctt      13380
gtattttcat ctgtgagaat aatcgctatg gaatgggaac gtctgttgag agagcggcag      13440
ccagcactga ttactacaag agaggcgatt tcattcctgg gctgagagta aggacacctg      13500
tggtggggcc ggggccaagg ccaaggccaa gggtatgtac cttgtgcaga cccttgacga      13560
tcttagaaac attggagagt ttcattctca tacaggagca ggtcatgtga aagtaaaatg      13620
gtttggggca gttggattca tgcttcgccc ctcccctgtt tattaccagg tggatggaat      13680
ggatatcctg tgcgtccgag aggcaacaag gtttgctgcc gcctatngta gatctgnnnn      13740
nnnnnnnnnn nnnnnnnnnn nnnnnnnnnn nnnnnnnnnn nnnnnnnnnn nnnnnnnnnn      13800
nnnnnnnnnn nnnnnnnnnn nnnnnnnnnn nnnnnnnnnn nnnnnnnnnn nnnnnnnnnn      13860
nnnnnnnnnn nnnnnnnnnn nnnnnnnnnn nnnnnnnnnn nnnnnnnnnn nnnnnnnnnn      13920
nnnnnnnnnn nnnnnnnnnn nnnnnnnnnn nnnnnnnnnn nnnnnnnnnn nnnnnnnnnn      13980
nnnnnnnnnn nnnnnnnnnn nnnnnnnnnn nnnnnnnnnn nnnnnnnnnn nnnnnnnnnn      14040
nnnnnnnnnn nnnnnnnnnn nnnnnnnnnn nnnnnnnnnn nnnnnnnnnn nnnnnnnnnn      14100
nnnnnnnnnn nnnnnnnnnn nnnnnnnnnn nnnnnnnnnn nnnnnnnnnn nnnnnnnnnn      14160
nnnnnnnnnn nnnnnnnnnn nnnnnnnnnn nnnnnnnnnn nnnnnnnnnn nnnnnnnnnn      14220
```

-continued

```
nnnnnnnnnn nnnnnnnnnn nnnnnnnnnn nnnnnnnnnn nnnnnnnnnn nnnnnnnnnn    14280
nnnnnnnnnn nnnnnnnnnn nnnnnnnnnn nnnnnnnnnn nnnnnnnnnn nnnnnnnnnn    14340
nnnnnnnnnn nnnnnnnnnn nnnnnnnnnn nnnnnnnnnn nnnnnnnnnn nnnnnnnnnn    14400
nnnnnnnnnn nnnnnnnnnn nnnnnnnnnn nnnnnnnnnn nnnnnnnnnn nnnnnnnnnn    14460
nnnnnnnnnn nnnnnnnnnn nnnnnnnnnn nnnnnnnnnn nnnnnnnnnn nnnnnnnnnn    14520
nnnnnnnnnn nnnnnnnnnn nnnnnnnnnn nnnnnnnnnn nnnnnnnnnn nnnnnnnnnn    14580
nnnnnnnnnn nnnnnnnnnn nnnnnnnnnn nnnnnnnnnn nnnnnnnnnn nnnnnnnnnn    14640
nnnnnnnnnn nnnnnnnnnn nnnnnnnnnn nnnnnnnnnn nnnnnnnnnn nnnnnnnnnn    14700
nnnnnnnnnn nnnnnnnnnn nnnnnnnnnn nnnnnnnnnn nnnnnnnnnn nnnnnnnnnn    14760
nnnnnnnnnn nnnnnnnnnn nnnnnnnnnn nnnnnnnnnn nnnnnnnnnn nnnnnnnnnn    14820
nnnnnnnnnn nnnnnnnnnn nnnnnnnnnn nnnnnnnnnn nnnnnnnnnn nnnnnnnnnn    14880
nnnnnnnnnn nnnnnnnnnn nnnnnnnnnn nnnnnnnnnn nnnnnnnnnn nnnnnnnnnn    14940
nnnnnnnnnn nnnnnnnnnn nnnnnnnnnn nnnnnnnnnn nnnnnnnnnn nnnnnnnnnn    15000
nnnnnnnnnn nnnnnnnnnn nnnnnnnnnn nnnnnnnnnn nnnnnnnnnn nnnnnnnnnn    15060
nnnnnnnnnn nnnnnnnnnn nnnnnnnnnn nnnnnnnnnn nnnnnnnnnn nnnnnnnnnn    15120
nnnnnnnnnn nnnnnnnnnn nnnnnnnnnn nnnnnnnnnn nnnnnnnnnn nnnnnnnnnn    15180
nnnnnnnnnn nnnnnnnnnn nnnnnnnnnn nnnnnnnnnn nnnnnnnnnn nnnnnnnnnn    15240
nnnnnnnnnn nnnnnnnnnn nnnnnnnnnn nnnnnnnnnn nnnnnnnnnn nnnnnnnnnn    15300
nnnnnnnnnn nnnnnnnnnn nnnnnnnnnn nnnnnnnnnn nnnnnnnnnn nnnnnnnnnn    15360
nnnnnnnnnn nnnnnnnnnn nnnnnnnnnn nnnnnnnnnn nnnnnnnnnn nnnnnnnnnn    15420
nnnnnnnnnn nnnnnnnnnn nnnnnnnnnn nnnnnnnnnn nnnnnnnnnn nnnnnnnnnn    15480
nnnnnnnnnn nnnnnnnnnn nnnnnnnnnn nnnnnnnnnn nnnnnnnnnn nnnnnnnnnn    15540
nnnnnnnnnn nnnnnnnnnn nnnnnnnnnn nnnnnnnnnn nnnnnnnnnn nnnnnnnnnn    15600
nnnnnnnnnn nnnnnnnnnn nnnnnnnnnn nnnnnnnnnn nnnnnnnnnn nnnnnnnnnn    15660
nnnnnnnnnn nnnnnnnnnn nnnnnnnnnn nnnnnnnnnn nnnnnnnnnn nnnnnnnnnn    15720
nnnnnnnnnn nnnnnncctt ttagtgttac ttcagatgat ataggcataa gatacattgg    15780
ttttgctggc tgtgcttctt tagggggact taagggagaa aggcaaggca catggatttc    15840
ctgcttggcg ctctgatgtc tcaaagtcta attatcacca cacacaccat ctctgctgtc    15900
cccacccatg tagtatacag gagcccaaat gggtgggaca agtgacactt ctttagaacc    15960
ttacatctaa atcaaagcag caagcaaaaa cttggcccct gttgtcggta atgccaggga    16020
agccatgtga ctcaccagtg tacggttttc tagaaaagac agaagcagtt attacagaat    16080
gttaggctgc gttctggtat tttgaaagta taacaacaac tctgccacgc ctatagtgac    16140
ataagcattg gtatgcccct tgtttcaga aacacacttc tgtatttcac ctcattggga    16200
caatccaacc ccatatcatg tttcatcacg ccgtccttgc tctactggaa ctgctcttac    16260
tgatcgatta ctacttttcc ctccccatag ttaccgtaca cgagaagaaa ttcaggaagt    16320
aagaagtaag agtgacccta ttatgcttct caaggacagg atggtgaaca gcaatcttgc    16380
cagtgtggaa gaactaaagg tacagtcact tgttcatggt ggtttgaagg ttggctttaa    16440
aagttgccac ccctgggtgg ccacagagtt tgtgtgggtt cctccaagcc cagaaagtga    16500
tgtcctggga cataaatagt tccatagttc caaagtccct tggggtgggg gcttttcctt    16560
```

```
tagtttcctc tattcaaaat tgtattactc ttcagatttc agattttggt ggactgtgaa    16620
ccaccatcac agtggcaaag cccccacagt agtatggttc ttttttccta aaagtatact    16680
gtggattttt aattcataaa atagatacac cctagaaatc tgtnnnnnnn nnnnnnnnnn    16740
nnnnnnnnnn nnnnnnnnnn nnnnnnnnnn nnnnnnnnnn nnnnnnnnnn nnnnnnnnnn    16800
nnnnnnnnnn nnnnnnnnnn nnnnnnnnnn nnnnnnnnnn nnnnnnnnnn nnnnnnnnnn    16860
nnnnnnnnnn nnnnnnnnnn nnnnnnnnnn nnnnnnnnnn nnnnnnnnnn nnnnnnnnnn    16920
nnnnnnnnnn nnnnnnnnnn nnnnnnnnnn nnnnnnnnnn nnnnnnnnnn nnnnnnnnnn    16980
nnnnnnnnnn nnnnnnnnnn nnnnnnnnnn nnnnnnnnnn nnnnnnnnnn nnnnnnnnnn    17040
nnnnnnnnnn nnnnnnnnnn nnnnnnnnnn nnnnnnnnnn nnnnnnnnnn nnnnnnnnnn    17100
nnnnnnnnnn nnnnnnnnnn nnnnnnnnnn nnnnnnnnnn nnnnnnnnnn nnnnnnnnnn    17160
nnnnnnnnnn nnnnnnnnnn nnnnnnnnnn nnnnnnnnnn nnnnnnnnnn nnnnnnnnnn    17220
nnnnnnnnnn nnnnnnnnnn nnnnnnnnnn nnnnnnnnnn nnnnnnnnnn nnnnnnnnnn    17280
nnnnnnnnnn nnnnnnnnnn nnnnnnnnnn nnnnnnnnnn nnnnnnnnnn nnnnnnnnnn    17340
nnnnnnnnnn nnnnnnnnnn nnnnnnnnnn nnnnnnnnnn nnnnnnnnnn nnnnnnnnnn    17400
nnnnnnnnnn nnnnnnnnnn nnnnnnnnnn nnnnnnnnnn nnnnnnnnnn nnnnnnnnnn    17460
nnnnnnnnnn nnnnnnnnnn nnnnnnnnnn nnnnnnnnnn nnnnnnnnnn nnnnnnnnnn    17520
nnnnnnnnnn nnnnnnnnnn nnnnnnnnnn nnnnnnnnnn nnnnnnnnnn nnnnnnnnnn    17580
nnnnnnnnnn nnnnnnnnnn nnnnnnnnnn nnnnnnnnnn nnnnnnnnnn nnnnnnnnnn    17640
nnnnnnnnnn nnnnnnnnnn nnnnnnnnnn nnnnnnnnnn nnnnnnnnnn nnnnnnnnnn    17700
nnnnnnnnnn nnnnnnnnnn nnnnnnnnnn nnnnnnnnnn nnnnnnnnnn nnnnnnnnnn    17760
nnnnnnnnnn nnnnnnnnnn nnnnnnnnnn nnnnnnnnnn nnnnnnnnnn nnnnnnnnnn    17820
nnnnnnnnnn nnnnnnnnnn nnnnnnnnnn nnnnnnnnnn nnnnnnnnnn nnnnnnnnnn    17880
nnnnnnnnnn nnnnnnnnnn nnnnnnnnnn nnnnnnnnnn nnnnnnnnnn nnnnnnnnnn    17940
nnnnnnnnnn nnnnnnnnnn nnnnnnnnnn nnnnnnnnnn nnnnnnnnnn nnnnnnnnnn    18000
nnnnnnnnnn nnnnnnnnnn nnnnnnnnnn nnnnnnnnnn nnnnnnnnnn nnnnnnnnnn    18060
nnnnnnnnnn nnnnnnnnnn nnnnnnnnnn nnnnnnnnnn nnnnnnnnnn nnnnnnnnnn    18120
nnnnnnnnnn nnnnnnnnnn nnnnnnnnnn nnnnnnnnnn nnnnnnnnnn nnnnnnnnnn    18180
nnnnnnnnnn nnnnnnnnnn nnnnnnnnnn nnnnnnnnnn nnnnnnnnnn nnnnnnnnnn    18240
nnnnnnnnnn nnnnnnnnnn nnnnnnnnnn nnnnnnnnnn nnnnnnnnnn nnnnnnnnnn    18300
nnnnnnnnnn nnnnnnnnnn nnnnnnnnnn nnnnnnnnnn nnnnnnnnnn nnnnnnnnnn    18360
nnnnnnnnnn nnnnnnnnnn nnnnnnnnnn nnnnnnnnnn                         18400

<210> SEQ ID NO 4
<211> LENGTH: 414
<212> TYPE: PRT
<213> ORGANISM: Human

<400> SEQUENCE: 4

Glu Thr Trp Gly His Pro Arg Arg Ala Ser Trp Val Val Arg Ser Arg
 1               5                  10                  15

Arg Cys Arg His Cys Leu Cys Phe Met Arg Lys Met Leu Ala Ala Val
                20                  25                  30

Ser Arg Val Leu Ser Gly Ala Ser Gln Lys Pro Ala Ser Arg Val Leu
            35                  40                  45
```

-continued

```
Val Ala Ser Arg Asn Phe Ala Asn Asp Ala Thr Phe Glu Ile Lys Lys
        50                  55                  60

Cys Asp Leu His Arg Leu Glu Glu Gly Pro Val Thr Thr Val Leu
 65                  70                  75                  80

Thr Arg Glu Asp Gly Leu Lys Tyr Tyr Arg Met Met Gln Thr Val Arg
                    85                  90                  95

Arg Met Glu Leu Lys Ala Asp Gln Leu Tyr Lys Gln Lys Ile Ile Arg
                100                 105                 110

Gly Phe Cys His Leu Cys Asp Gly Gln Glu Ala Cys Cys Val Gly Leu
                115                 120                 125

Glu Ala Gly Ile Asn Pro Thr Asp His Leu Ile Thr Ala Tyr Arg Ala
        130                 135                 140

His Gly Phe Thr Phe Thr Arg Gly Leu Ser Val Arg Glu Ile Leu Ala
145                 150                 155                 160

Glu Leu Thr Gly Arg Lys Gly Gly Cys Ala Lys Gly Lys Gly Gly Ser
                    165                 170                 175

Met His Met Tyr Ala Lys Asn Phe Tyr Gly Gly Asn Gly Ile Val Gly
                180                 185                 190

Ala Gln Val Pro Leu Gly Ala Gly Ile Ala Leu Ala Cys Lys Tyr Asn
        195                 200                 205

Gly Lys Asp Glu Val Cys Leu Thr Leu Tyr Gly Asp Gly Ala Ala Asn
    210                 215                 220

Gln Gly Gln Ile Phe Glu Ala Tyr Asn Met Ala Ala Leu Trp Lys Leu
225                 230                 235                 240

Pro Cys Ile Phe Ile Cys Glu Asn Asn Arg Tyr Gly Met Gly Thr Ser
                    245                 250                 255

Val Glu Arg Ala Ala Ser Thr Asp Tyr Tyr Lys Arg Gly Asp Phe
                260                 265                 270

Ile Pro Gly Leu Arg Val Asp Gly Met Asp Ile Leu Cys Val Arg Glu
        275                 280                 285

Ala Thr Arg Phe Ala Ala Ala Tyr Cys Arg Ser Gly Lys Gly Pro Ile
290                 295                 300

Leu Met Glu Leu Gln Thr Tyr Arg Tyr His Gly His Ser Met Ser Asp
305                 310                 315                 320

Pro Gly Val Ser Tyr Arg Thr Arg Glu Glu Ile Gln Glu Val Arg Ser
                325                 330                 335

Lys Ser Asp Pro Ile Met Leu Leu Lys Asp Arg Met Val Asn Ser Asn
                340                 345                 350

Leu Ala Ser Val Glu Glu Leu Lys Glu Ile Asp Val Glu Val Arg Lys
            355                 360                 365

Glu Ile Glu Asp Pro Ala Gln Phe Ala Ala Asp Pro Glu Pro Pro
    370                 375                 380

Leu Glu Glu Leu Gly Tyr His Ile Tyr Ser Ser Asp Pro Pro Phe Glu
385                 390                 395                 400

Val Arg Gly Ala Asn Gln Trp Ile Lys Phe Lys Ser Val Ser
                    405                 410
```

<210> SEQ ID NO 5
<211> LENGTH: 390
<212> TYPE: PRT
<213> ORGANISM: Human

<400> SEQUENCE: 5

```
Met Arg Lys Met Leu Ala Ala Val Ser Arg Val Leu Ser Gly Ala Ser
 1               5                  10                  15
```

-continued

```
Gln Lys Pro Ala Ser Arg Val Leu Val Ala Ser Arg Asn Phe Ala Asn
             20                  25                  30
Asp Ala Thr Phe Glu Ile Lys Lys Cys Asp Leu His Arg Leu Glu Glu
         35                  40                  45
Gly Pro Pro Val Thr Thr Val Leu Thr Arg Glu Asp Gly Leu Lys Tyr
     50                  55                  60
Tyr Arg Met Met Gln Thr Val Arg Arg Met Glu Leu Lys Ala Asp Gln
 65                  70                  75                  80
Leu Tyr Lys Gln Lys Ile Ile Arg Gly Phe Cys His Leu Cys Asp Gly
                 85                  90                  95
Gln Glu Ala Cys Cys Val Gly Leu Glu Ala Gly Ile Asn Pro Thr Asp
            100                 105                 110
His Leu Ile Thr Ala Tyr Arg Ala His Gly Phe Thr Phe Thr Arg Gly
        115                 120                 125
Leu Ser Val Arg Glu Ile Leu Ala Glu Leu Thr Gly Arg Lys Gly Gly
    130                 135                 140
Cys Ala Lys Gly Lys Gly Gly Ser Met His Met Tyr Ala Lys Asn Phe
145                 150                 155                 160
Tyr Gly Gly Asn Gly Ile Val Gly Ala Gln Val Pro Leu Gly Ala Gly
                165                 170                 175
Ile Ala Leu Ala Cys Lys Tyr Asn Gly Lys Asp Glu Val Cys Leu Thr
            180                 185                 190
Leu Tyr Gly Asp Gly Ala Ala Asn Gln Gly Gln Ile Phe Glu Ala Tyr
        195                 200                 205
Asn Met Ala Ala Leu Trp Lys Leu Pro Cys Ile Phe Ile Cys Glu Asn
    210                 215                 220
Asn Arg Tyr Gly Met Gly Thr Ser Val Glu Arg Ala Ala Ala Ser Thr
225                 230                 235                 240
Asp Tyr Tyr Lys Arg Gly Asp Phe Ile Pro Gly Leu Arg Val Asp Gly
                245                 250                 255
Met Asp Ile Leu Cys Val Arg Glu Ala Thr Arg Phe Ala Ala Ala Tyr
            260                 265                 270
Cys Arg Ser Gly Lys Gly Pro Ile Leu Met Glu Leu Gln Thr Tyr Arg
        275                 280                 285
Tyr His Gly His Ser Met Ser Asp Pro Gly Val Ser Tyr Arg Thr Arg
    290                 295                 300
Glu Glu Ile Gln Glu Val Arg Ser Lys Ser Asp Pro Ile Met Leu Leu
305                 310                 315                 320
Lys Asp Arg Met Val Asn Ser Asn Leu Ala Ser Val Glu Glu Leu Lys
                325                 330                 335
Glu Ile Asp Val Glu Val Arg Lys Glu Ile Glu Asp Ala Ala Gln Phe
            340                 345                 350
Ala Thr Ala Asp Pro Glu Pro Leu Glu Glu Leu Gly Tyr His Ile
        355                 360                 365
Tyr Ser Ser Asp Pro Pro Phe Glu Val Arg Gly Ala Asn Gln Trp Ile
    370                 375                 380
Lys Phe Lys Ser Val Ser
385                 390

<210> SEQ ID NO 6
<211> LENGTH: 390
<212> TYPE: PRT
<213> ORGANISM: Mus musculus
```

```
<400> SEQUENCE: 6

Met Arg Lys Met Leu Ala Ala Val Ser Arg Val Leu Ala Gly Ser Ala
1               5                   10                  15

Gln Lys Pro Ala Ser Arg Val Leu Val Ala Ser Arg Asn Phe Ala Asn
            20                  25                  30

Asp Ala Thr Phe Glu Ile Lys Lys Cys Asp Leu His Arg Leu Glu Glu
            35                  40                  45

Gly Pro Pro Val Thr Thr Val Leu Thr Arg Glu Asp Gly Leu Lys Tyr
    50                  55                  60

Tyr Arg Met Met Gln Thr Val Arg Arg Met Glu Leu Lys Ala Asp Gln
65                  70                  75                  80

Leu Tyr Lys Gln Lys Ile Ile Arg Gly Phe Cys His Leu Cys Asp Gly
                85                  90                  95

Gln Glu Ala Cys Cys Val Gly Leu Glu Ala Gly Ile Asn Pro Thr Asp
            100                 105                 110

His Leu Ile Thr Ala Tyr Arg Ala His Gly Phe Thr Phe Thr Arg Gly
            115                 120                 125

Leu Pro Val Arg Ala Ile Leu Ala Glu Leu Thr Gly Arg Arg Gly Gly
    130                 135                 140

Cys Ala Lys Gly Lys Gly Gly Ser Met His Met Tyr Ala Lys Asn Phe
145                 150                 155                 160

Tyr Gly Gly Asn Gly Ile Val Gly Ala Gln Val Pro Leu Gly Ala Gly
                165                 170                 175

Ile Ala Leu Ala Cys Lys Tyr Asn Gly Lys Asp Glu Val Cys Leu Thr
            180                 185                 190

Leu Tyr Gly Asp Gly Ala Ala Asn Gln Gly Gln Ile Phe Glu Ala Tyr
    195                 200                 205

Asn Met Ala Ala Leu Trp Lys Leu Pro Cys Ile Phe Ile Cys Glu Asn
210                 215                 220

Asn Arg Tyr Gly Met Gly Thr Ser Val Glu Arg Ala Ala Ala Ser Thr
225                 230                 235                 240

Asp Tyr Tyr Lys Arg Gly Asp Phe Ile Pro Gly Leu Arg Val Asp Gly
                245                 250                 255

Met Asp Ile Leu Cys Val Arg Glu Ala Thr Lys Phe Ala Ala Ala Tyr
            260                 265                 270

Cys Arg Ser Gly Lys Gly Pro Ile Leu Met Glu Leu Gln Thr Tyr Arg
    275                 280                 285

Tyr His Gly His Ser Met Ser Asp Pro Gly Val Ser Tyr Arg Thr Arg
290                 295                 300

Glu Glu Ile Gln Glu Val Arg Ser Lys Ser Asp Pro Ile Met Leu Leu
305                 310                 315                 320

Lys Asp Arg Met Val Asn Ser Asn Leu Ala Ser Val Glu Glu Leu Lys
                325                 330                 335

Glu Ile Asp Val Glu Val Arg Lys Glu Ile Glu Asp Ala Ala Gln Phe
            340                 345                 350

Ala Thr Ala Asp Pro Glu Pro Pro Leu Glu Glu Leu Gly Tyr His Ile
    355                 360                 365

Tyr Ser Ser Asp Pro Pro Phe Glu Val Arg Gly Ala Asn Gln Trp Ile
    370                 375                 380

Lys Phe Lys Ser Val Ser
385                 390
```